(12) United States Patent
Srinivasan et al.

(10) Patent No.: US 11,357,929 B2
(45) Date of Patent: Jun. 14, 2022

(54) NEEDLE STORAGE MAGAZINE ASSEMBLY

(71) Applicant: Embecta Corp., Andover, MA (US)

(72) Inventors: Sudarsan Srinivasan, North Brunswick, NJ (US); David R. Schiff, Highland Park, NJ (US); Stephan Lawson, Upper Darby, PA (US); Amit Uday Limaye, Wayne, NJ (US); Matthew E. Zuschlag, Randolph, NJ (US); Donald Vanroyen, Philadelphia, PA (US)

(73) Assignee: Embecta Corp., Andover, MA (US)

( * ) Notice: Subject to any disclaimer, the term of this patent is extended or adjusted under 35 U.S.C. 154(b) by 0 days.

(21) Appl. No.: 17/033,859

(22) Filed: Sep. 27, 2020

(65) Prior Publication Data
US 2021/0016018 A1 Jan. 21, 2021

Related U.S. Application Data

(60) Division of application No. 16/096,964, filed as application No. PCT/US2017/029942 on Apr. 27, (Continued)

(51) Int. Cl.
*A61M 5/32* (2006.01)
*A61M 5/34* (2006.01)
(Continued)

(52) U.S. Cl.
CPC ............ *A61M 5/3298* (2013.01); *A61M 5/00* (2013.01); *A61M 5/002* (2013.01); *A61M 5/321* (2013.01);
(Continued)

(58) Field of Classification Search
CPC .. A61M 2005/2474; A61M 2039/1072; A61M 2039/1077; A61M 5/002;
(Continued)

(56) References Cited

U.S. PATENT DOCUMENTS 2,778,360 A * 1/1957 Miskel ................ A61M 5/2448
604/87
3,884,229 A * 5/1975 Raines .................... A61M 5/24
604/242
(Continued)

FOREIGN PATENT DOCUMENTS

EP 2119423 A1 11/2009
JP 2000-102614 A 4/2000
(Continued)

OTHER PUBLICATIONS

International Search Report dated Sep. 13, 2017, which issued in corresponding PCT Patent Application Mo. PCT/US2017/029942.
(Continued)

*Primary Examiner* — Rebecca E Eisenberg
(74) *Attorney, Agent, or Firm* — Greenberg Traurig, LLP; David J. Dykeman; Roman Fayerberg

(57) ABSTRACT

A magazine assembly (1) that stores a plurality of needles (56) configured to engage a medication pen (2) via an adapter (4) for medication delivery, the magazine assembly (1) comprising a magazine housing (20) enclosing a plurality of hub chambers (22) each enclosing one of a plurality of needle hubs (50), a connector (28) in each of the plurality of hub chambers (22), each connector (28) engages one of the plurality of needle hubs (50), and a plurality of enclosures (30) each sealing the plurality of hub chambers (22), wherein a selected enclosure of the plurality of enclosures (30) is removed to expose a selected needle hub (52) of the plurality of needle hubs (50), the adapter (4) attaches to the medication pen (2) to engage the selected needle hub (52) while disengaging the selected needle hub (52) from the hub chamber (22), and the selected needle hub (52) is removed from the magazine housing (20) to prepare the medication pen (2) for medication delivery.

19 Claims, 20 Drawing Sheets

Related U.S. Application Data 2017, now Pat. No. 10,828,428, which is a continuation-in-part of application No. PCT/US2017/025471, filed on Mar. 31, 2017.

(60) Provisional application No. 62/328,697, filed on Apr. 28, 2016.

(51) Int. Cl.
*A61M 5/00* (2006.01)
*A61M 39/10* (2006.01)
*A61M 5/24* (2006.01)

(52) U.S. Cl.
CPC ........ *A61M 5/3205* (2013.01); *A61M 5/3293* (2013.01); *A61M 5/345* (2013.01); *A61M 5/347* (2013.01); *A61M 5/348* (2013.01); *A61M 2005/2474* (2013.01); *A61M 2039/1072* (2013.01); *A61M 2039/1077* (2013.01)

(58) Field of Classification Search
CPC .. A61M 5/3293; A61M 5/3298; A61M 5/345; A61M 5/347; A61M 5/348; A61M 5/34; A61M 5/288; A61M 5/285; A61J 1/2006; A61J 1/2003; A61J 1/201; A61J 1/1406
See application file for complete search history.

(56) References Cited

U.S. PATENT DOCUMENTS

| | | | |
|---|---|---|---|
| 3,895,633 A * | 7/1975 | Bartner | A61M 5/178 604/192 |
| 4,998,927 A | 3/1991 | Vaillancourt | |
| 5,829,589 A | 11/1998 | Nguyen | |
| 5,931,817 A | 8/1999 | Nguyen | |
| 6,346,094 B2 | 2/2002 | West | |
| 7,134,550 B2 | 11/2006 | Groth | |
| 8,012,132 B2 | 9/2011 | Lum | |
| 8,876,780 B2 | 11/2014 | Bruehwiler et al. | |
| 9,060,758 B2 | 6/2015 | Dasbach | |
| 9,101,724 B2 | 8/2015 | Chapin et al. | |
| 9,107,988 B2 | 8/2015 | Bruehwiler et al. | |
| 9,216,253 B2 | 12/2015 | Spool | |
| 9,381,303 B2 | 7/2016 | Abhijitsinh et al. | |
| 9,427,514 B2 | 8/2016 | Bruehwiler | |
| 9,717,860 B2 | 8/2017 | Bruehwiler et al. | |
| 10,029,042 B2 | 7/2018 | Searle et al. | |
| 10,350,371 B2 | 7/2019 | Bates | |
| 2001/0014792 A1 | 8/2001 | West | |
| 2005/0084631 A1 | 4/2005 | Anderson | |
| 2010/0217206 A1 | 8/2010 | Lum et al. | |
| 2011/0068034 A1 | 3/2011 | Hwang et al. | |
| 2011/0106046 A1 | 5/2011 | Hiranuma et al. | |
| 2012/0041390 A1 | 2/2012 | Spool et al. | |
| 2012/0065612 A1 | 3/2012 | Stout et al. | |
| 2014/0076758 A1 | 3/2014 | Dasbach et al. | |
| 2014/0299622 A1 | 10/2014 | Hofmann et al. | |
| 2015/0328412 A1 | 11/2015 | Bates et al. | |
| 2018/0036478 A1 * | 2/2018 | Yang | A61M 5/158 |

FOREIGN PATENT DOCUMENTS

| | | |
|---|---|---|
| JP | 2011-063445 A | 3/2011 |
| JP | 2012-050820 A | 3/2012 |
| JP | 2014-532532 A | 12/2014 |
| JP | 2016-505336 A | 2/2016 |

OTHER PUBLICATIONS

Written Opinion of the International Searching Authority dated Sep. 13, 2017, which issued in the corresponding Application No. PCT/US2017/029942.

Japanese Office Action dated Mar. 2, 2021, which issued in the corresponding Japanese Patent Application No. 2018-554362, including Eng. translation.

* cited by examiner

NEEDLE STORAGE MAGAZINE ASSEMBLY

This application is a divisional application of U.S. patent application Ser. No. 16/096,964, filed on Oct. 26, 2018, which is a 371 application of PCT/US2017/029042, filed on Apr. 27, 2017, which claims the benefit of U.S. Provisional Patent Application Ser. 62/328,697, filed on Apr. 28, 2016, and claims the benefit of PCT/US2017/025471, filed on Mar. 31, 2017, all of which are hereby incorporated by reference in their entireties.

FIELD

Various exemplary embodiments of the invention relate to needle storage for medication pens.

BACKGROUND

Medication pens are typically used to inject medication into a patient. A person who must periodically self-inject doses of medication will typically carry a medication pen and several single-use pen needles. A medication pen is designed for safety and sterility. However, inefficiencies and inconveniences arise.

SUMMARY OF THE INVENTION

It is an aspect of the present invention to provide a magazine assembly that stores a plurality of needles configured to engage a medication pen via an adapter for medication delivery. Such a magazine assembly provides advantages in minimizing the size of pen needle packaging, minimizing the volume of plastic used to manufacture components and grouping together a number of pen needles making them easy to use and carry. Such advantages are provided in a magazine housing, as well as in the adapter.

Having a magazine of needles available for medication delivery reduces needle reuse. Needle reuse is undesired for at least the following reasons. The needle dulls after a single use and so subsequent use may cause pain to the patient. Multiple needle use can also reduce the strength of the needle tip which may cause a potential fracture. Also, needle reuse increases sanitary concerns and health risks to the patient.

The needle assembly of the present invention advantageously reduces reuse for at least the following reasons. Although patients may desire to financially benefit from using a needle multiple times, the needle assembly is configured to prevent each of the plurality of needles from being used more than once. Convenience is another reason patients reuse needles. Patients may also be concerned about not having another needle available for use or not having access to supplies. However, the needle assembly conveniently provides multiple needles so that an unused needle is more readily available.

The foregoing and/or other aspects of the present invention can be achieved by providing a magazine assembly that stores a plurality of needles configured to engage a medication pen via an adapter for medication delivery, the magazine assembly comprising a magazine housing enclosing a plurality of hub chambers each enclosing one of a plurality of needle hubs, a connector in each of the plurality of hub chambers, each connector engaging one of the plurality of needle hubs, and a plurality of enclosures sealing the plurality of hub chambers, wherein a selected enclosure of the plurality of enclosures is removed to expose a selected needle hub of the plurality of needle hubs, the adapter attaches to the medication pen to engage the selected needle hub while disengaging the selected needle hub from the hub chamber, and the selected needle hub is removed from the magazine housing to prepare the medication pen for medication delivery.

Preferably, the adapter includes an adapter body, and a proximal end of the adapter body includes threads that are configured to engage the medication pen. A distal end of the adapter body includes an opening, and the opening is configured to engage one of the plurality of needle hubs. The adapter includes an adapter septum wherein the adapter septum is closed when the adapter does not engage the selected needle hub and the adapter septum is open when the adapter engages the selected needle hub. A proximal end of the selected needle hub compresses the adapter septum and provides a sealing surface. The adapter also includes an adapter cannula that is configured to pierce a septum of the medication pen to establish fluid communication with the medication pen and a distal end of the adapter cannula is disposed in the adapter septum.

Preferably, the magazine housing includes two magazine arrays disposed opposite each other, each magazine array includes the plurality of hub chambers. The magazine housing further comprises a storage bin that stores used needle hubs, and the storage bin is disposed between the two magazine arrays. Each magazine array preferably includes eight hub chambers and the enclosures include a foil tab. The storage bin includes an adapter chamber that is configured to store the adapter, and when the adapter is disposed in the adapter chamber of the storage bin, the adapter seals the storage bin. The adapter chamber is configured to engage an end cap and is sealed by one of the plurality of enclosures prior to use.

The foregoing and/or other aspects of the present invention can further be achieved by providing an adapter configured to engage a medication pen for medication delivery, the adapter comprising an adapter body having a proximal end and a distal end, an adapter septum disposed between the proximal end and the distal end of the adapter body, and an adapter cannula being fixed to the adapter body and partially disposed within the adapter septum, wherein when a needle hub is not engaged to the adapter body, the adapter septum is closed, and when the needle hub is engaged to the adapter body, the needle hub compresses the adapter septum and causes the adapter cannula to pierce the adapter septum to establish fluid communication with the needle hub.

Additionally, the foregoing and/or other aspects of the present invention can be achieved by providing a magazine that stores a plurality of needles configured to engage a medication pen for medication delivery, the magazine comprising a magazine housing enclosing a plurality of hub chambers each enclosing one of a plurality of needle hubs, a connector in each of the plurality of hub chambers, each connector engaging one of the plurality of needle hubs, and a plurality of enclosures sealing the plurality of hub chambers, wherein a selected enclosure of the plurality of enclosures is removed to expose a selected needle hub of the plurality of needle hubs, the medication pen engages the selected needle hub while disengaging the selected needle hub from the hub chamber, and the selected needle hub is removed from the magazine housing to prepare the medication pen for medication delivery.

The foregoing and/or other aspects of the present invention can also be achieved by a method of using a plurality of needles in a magazine assembly, the plurality of needles being configured to engage a medication pen via an adapter for medication delivery, the method comprising removing a selected enclosure of a plurality of enclosures to expose a selected needle hub of a plurality of needle hubs in a magazine housing, attaching the adapter to the medication pen, engaging the adapter to the selected needle hub, and disengaging the selected needle hub from the magazine housing to prepare the medication pen for medication delivery.

The features of the invention are further attained by providing a magazine assembly for a plurality of needle hubs where the assembly includes a housing having a plurality of chambers, a connector in each of the chambers, and a needle hub with a proximal end configured for coupling to the connector by a snap fit. The needle hub has a cannula extending from a proximal end. The connector within the chamber in one embodiment can include one or more legs that are able to grip an outer surface of the needle hub to retain the needle hub within the chamber while allowing separation without damaging the needle hub. The legs can include a coupling tab that engages a flange or other member on the needle hub by a snap fit or interference fit. An adapter can be provided for coupling the needle hub to a delivery pen. The adapter has a proximal end for connecting to the delivery pen and distal end for coupling to the needle hub. The distal end of the adapter can include a connecting assembly for engaging the proximal end of the needle hub with a gripping force greater than a gripping force of the needle hub relative to the connector of the hub chamber whereby the needle hub can be separated from the connector in the chamber.

The magazine housing can also include an internal cavity, an opening communicating with the internal cavity and a disconnecting assembly. The disconnecting assembly is able to couple to the distal end of a used needle hub with a gripping force greater than gripping force of the needle hub relative to the adapter or delivery device whereby the needle hub can be separated from the adapter or delivery device. The disconnecting assembly can include at least one and generally a plurality of legs that are able to grip the distal end of the needle hub to separate the needle hub from the adapter and retain the used needle hub within the cavity of the housing.

Additional and/or other aspects and advantages of the present invention will be set forth in the description that follows, or will be apparent from the description, or may be learned by practice of the invention.

BRIEF DESCRIPTION OF THE DRAWINGS

The above aspects and features of the present invention will be more apparent from the description for the exemplary embodiments of the present invention taken with reference to the accompanying drawings, in which.

DETAILED DESCRIPTION OF EXEMPLARY EMBODIMENTS

Figure 1:
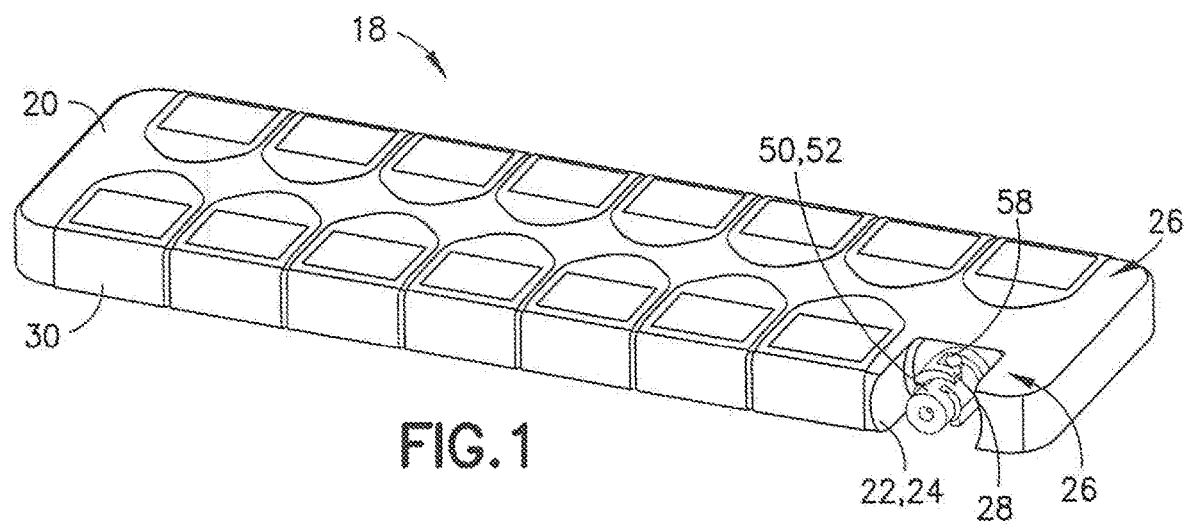
FIG. 1 illustrates a left perspective view of an exemplary magazine.

According to one embodiment, FIG. 1 illustrates a magazine 18 that stores a plurality of needles or cannulas used by a medication pen for medication delivery. The magazine 18 includes a magazine housing 20, a plurality of hub chambers 22 each including a connector 28, a selected hub chamber 24, and magazine arrays 26. The magazine housing 20 is in the shape of a credit card and encloses each of the plurality of needles or cannulas.

The magazine housing 20 includes two magazine arrays 26. Each of the magazine arrays 26 carries one of a plurality of needle hubs 50 in each of the plurality of hub chambers 22. Each magazine array 26 can includes eight hub chambers 22, although more or fewer are contemplated. The magazine arrays 26 are opposite one another in a longitudinal direction. The plurality of needle hubs 50 are inline and adjacent to one another. Such a configuration advantageously provides a small, compact, and optimized arrangement of the plurality of needle hubs 50 and allows the magazine 18 to be made from a minimal amount of material. Additionally, the plurality of needle hubs 50 are individually disposed in each of the plurality of hub chambers 22 to advantageously provide a separate cavity for each needle hub 50.

Each of the plurality of hub chambers 22 includes the connector 28 which secures each of the plurality of needle hubs 50. The connector 28 is preferably a quarter-turn bayonet connection, although a push-pull detent connector can also be used. Further details of the connector 28 are described below.

Each of the plurality of hub chambers 22 is enclosed by a peel tab or enclosure 30. The peel tabs 30 can be foil tabs. Each peel tab 30 individually seals and provides a sterile environment for one of the plurality of needle hubs 50 disposed in the plurality of hub chambers 22. Such a configuration advantageously provides independent access to each of the plurality of needle hubs 50. As a result, one of the plurality of needle hubs 50 can be used without altering the sterile environment of the remaining needle hubs 50.

FIG. 1 also illustrates one of the plurality of peel tabs 30 removed to expose a selected hub chamber 24 of the plurality of hub chambers 22. The selected hub chamber 24 includes a selected needle hub 52 ready for use.

Figure 2:
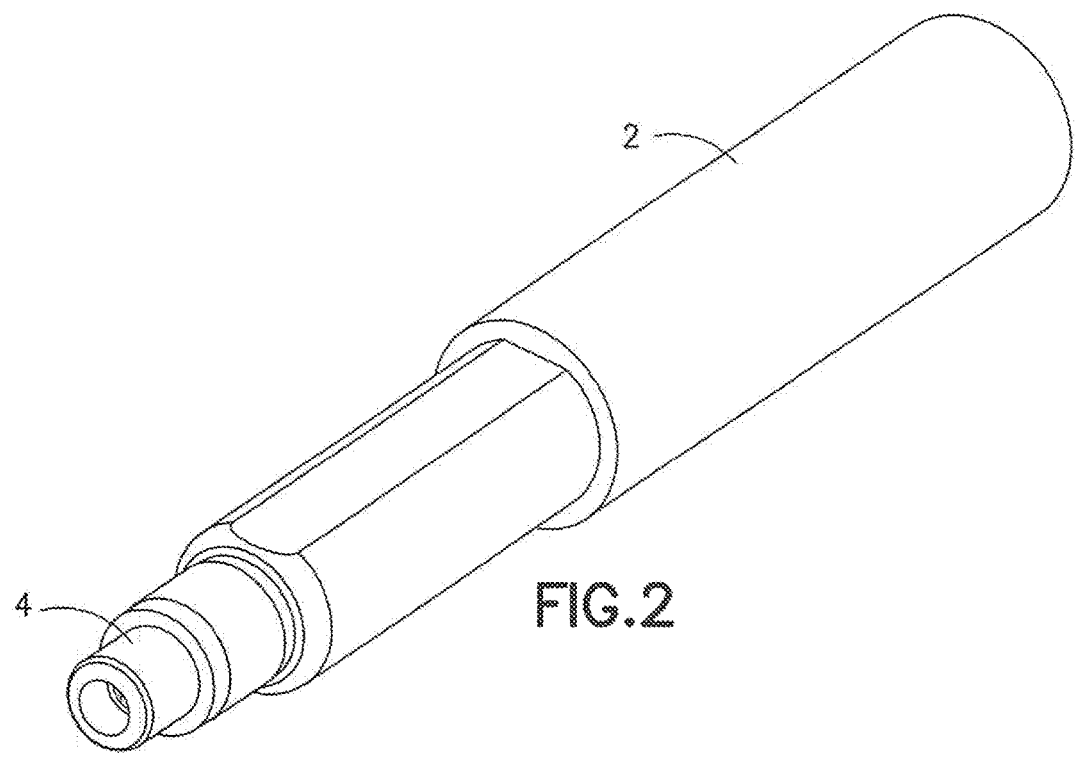
FIG. 2 illustrates the right perspective view of an exemplary adapter connected to a medication pen.
Figure 3:
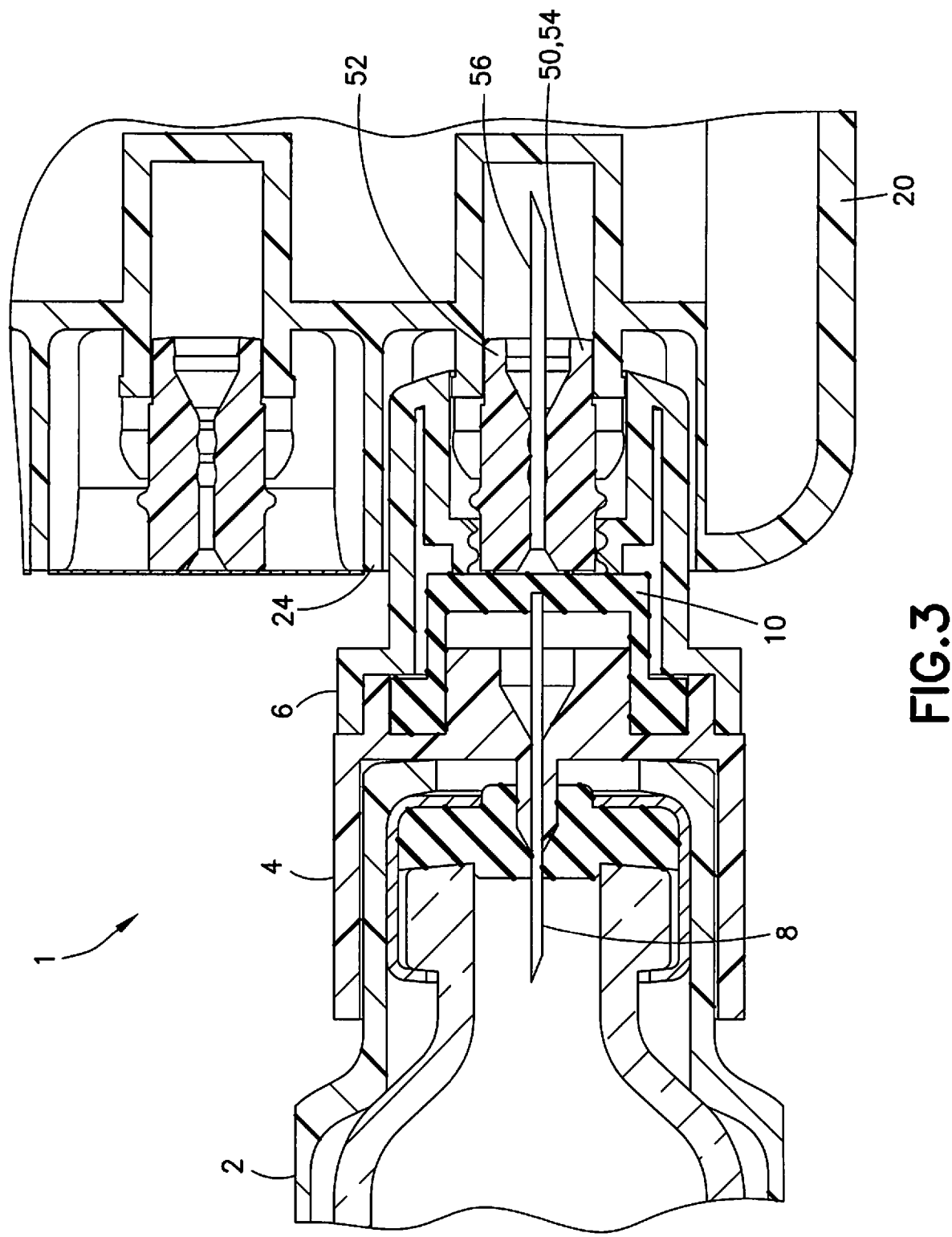
FIG. 3 illustrates a partial cross sectional view of the medication pen of FIG. 2 beginning to connect to a needle hub in a magazine housing.
Figure 4:
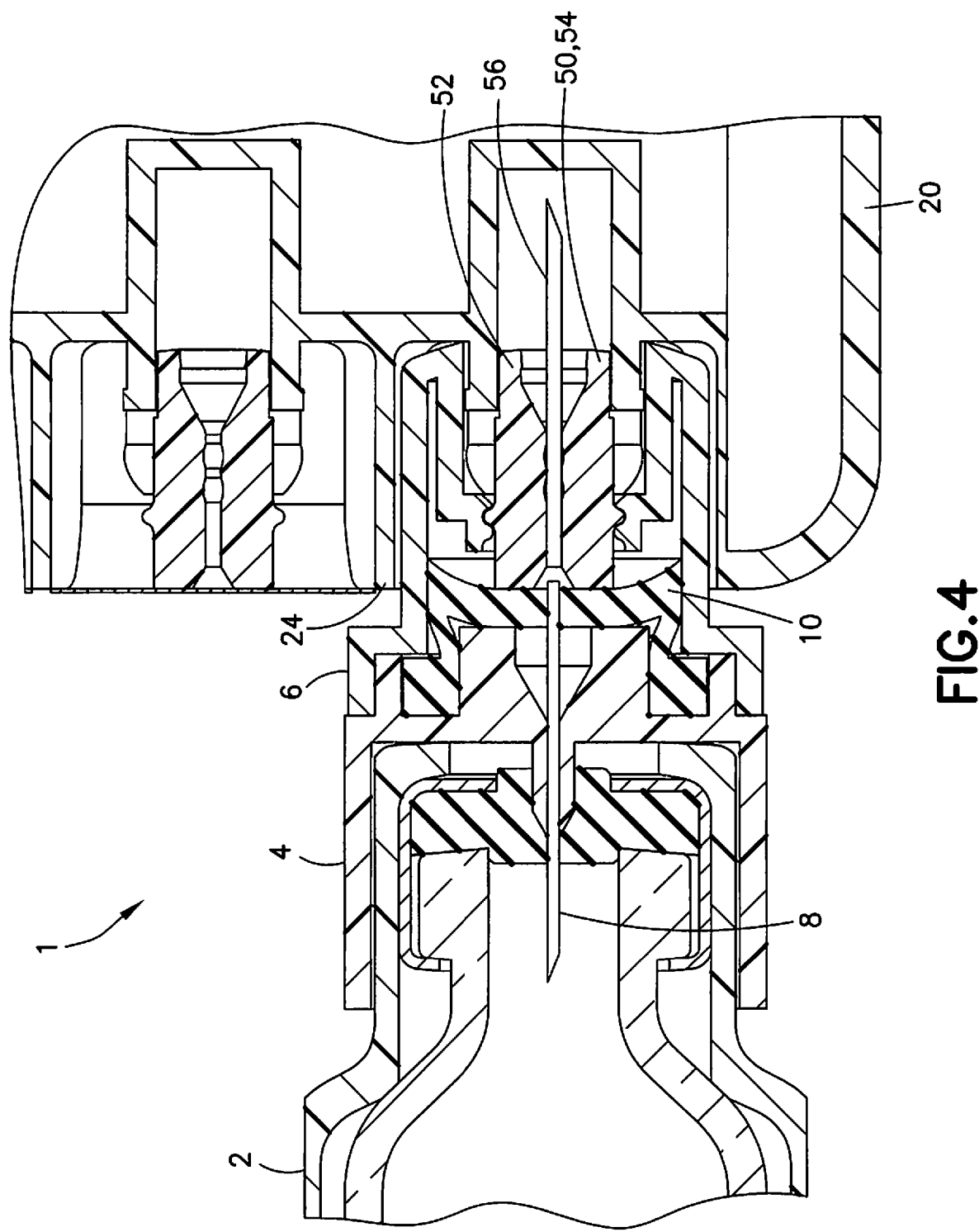
FIG. 4 illustrates a partial cross sectional view of the medication pen of FIG. 2 fully engaged to a needle hub in the magazine housing.

FIG. 2, according to one embodiment, illustrates a medication pen 2 connected to an adapter 4. The adapter 4 is attachable to a standard reusable medication pen 2 (i.e. pen injector). The components of the adapter 4 are illustrated in FIGS. 3 and 4. FIG. 3 illustrates the adapter 4 connected to the medication pen 2 and beginning to engage the selected needle hub 52. The adapter 4 includes an adapter body 6, an adapter cannula 8 and an adapter septum 10. The adapter body 6 can be a two piece press-fit assembly that encloses and secures the adapter septum 10. A proximal end of the adapter body 6 includes threads that are configured to engage threads on the medication pen 2. A distal end of the adapter body 6 includes an opening. The opening is configured to engage one of a plurality of needle hubs 50.

The adapter cannula 8 is fixed to the adapter body 6. The adapter cannula 8 is disposed in the proximal end of the adapter body 6 and is configured to pierce a septum (not shown) of the medication pen 2 to establish fluid communication with the medication pen 2. A distal end of the adapter cannula 8 is disposed in the adapter septum 10. Operation of the adapter cannula 8 with the adapter septum 10 is described below.

The adapter septum 10 regulates the flow of medicament between the medication pen 2 and the selected needle hub 52. The adapter septum 10 is closed in its natural state. As illustrated in FIG. 3, the adapter septum 10 partially engages the adapter cannula 8 at its distal end in the closed position. Since the selected needle hub 52 in not fully engaged with the adapter 4, the adapter septum 10 remains in the closed position. That is, the adapter septum 10 of FIG. 3 is in its natural state.

The adapter septum 10 can include a preformed opening for the adapter cannula 8 to pierce. Alternately, a sharpened distal end of the adapter cannula 8 pierces the adapter septum 10 to establish fluid communication. The adapter septum 10 is preferably made of silicon rubber.

FIG. 4 illustrates the adapter septum 10 in an open position. The selected needle hub 52 is fixed to the adapter body 6 via a push-pull detent although other methods are contemplated. When the selected needle hub 52 is fixed to the adapter body 6, the selected needle hub 52 applies an axial force to the adapter septum 10. The axial force causes the adapter septum 10 to flex (or compress) and allows the adapter cannula 8 to pierce the adapter septum 10 and extend into the selected needle hub 52. The axial force also establishes a sealing surface to prevent a leak path at an interface between a proximal end of the selected needle hub 52 and a distal surface of the adapter septum 10. Accordingly, the selected needle hub 52 is now in fluid communication with the medication pen 2.

Figure 5:
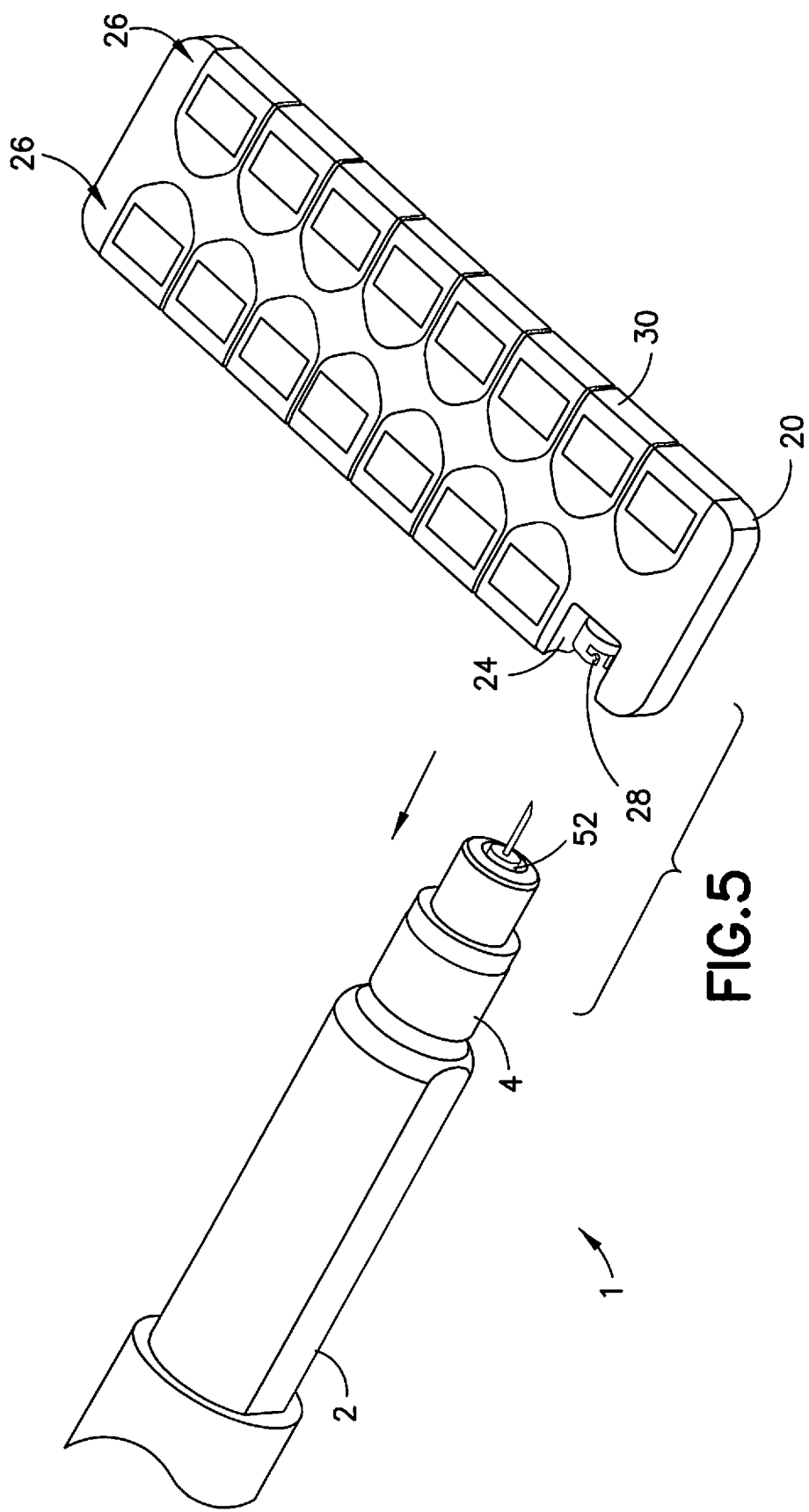
FIG. 5 illustrates a right perspective view of the magazine assembly where the medication pen engaged to the needle hub is being removed from the magazine housing.

According to one embodiment, FIG. 5 illustrates the magazine assembly 1 where the selected needle hub 52 is connected to the medication pen 2 via the adapter 4 and is removed from the magazine 18. Specifically, the selected needle hub 52 disengages the connector 28 in the selected hub chamber 24 of the magazine housing 20. Each of the plurality of needle hubs 50 cannot be easily removed from the magazine housing 20 without using the adapter 4. The medication pen 2 is now ready for medication delivery.

Figure 6:
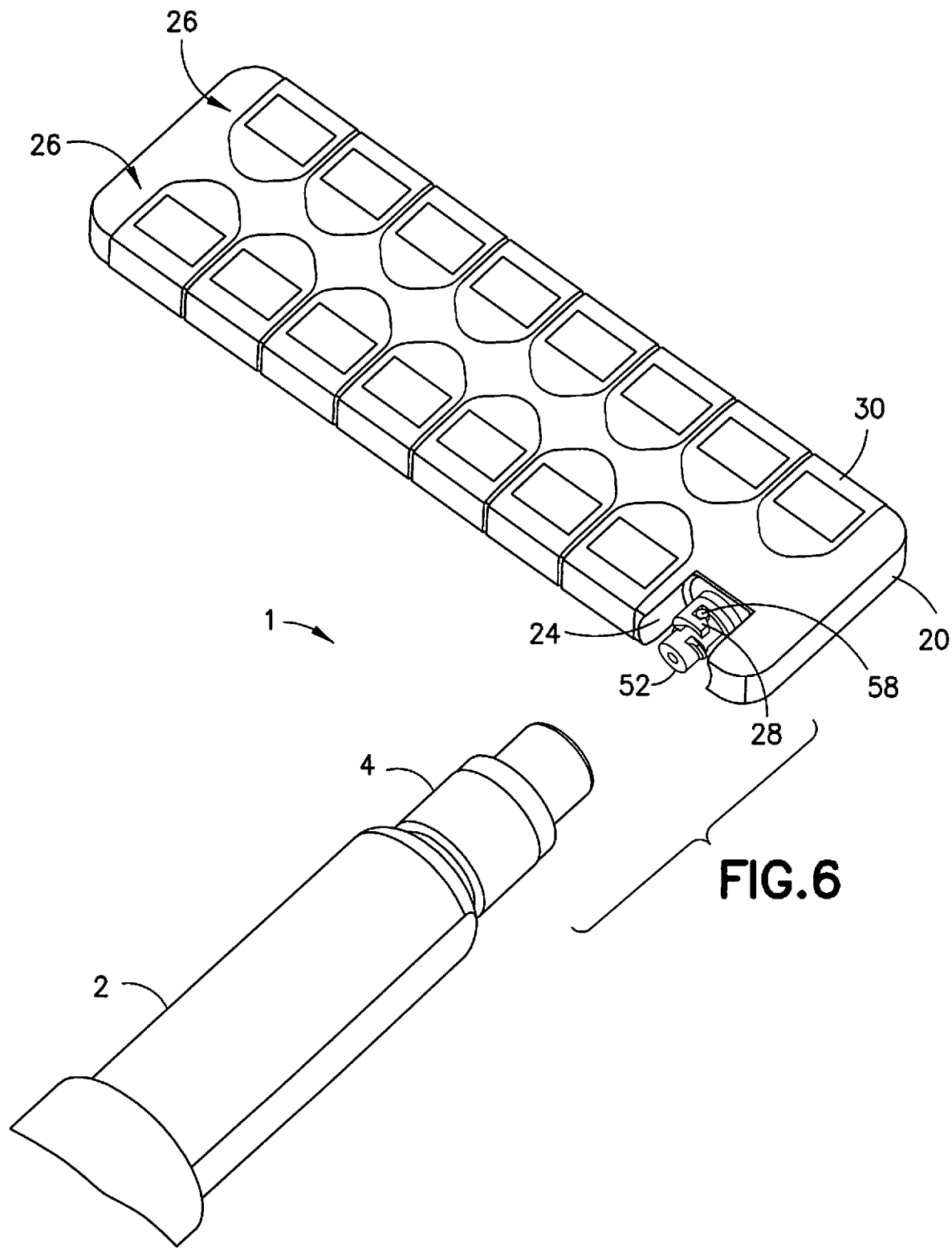
FIG. 6 illustrates a right perspective view of the magazine assembly where the medication pen returns the needle hub to the magazine housing.
Figure 7:
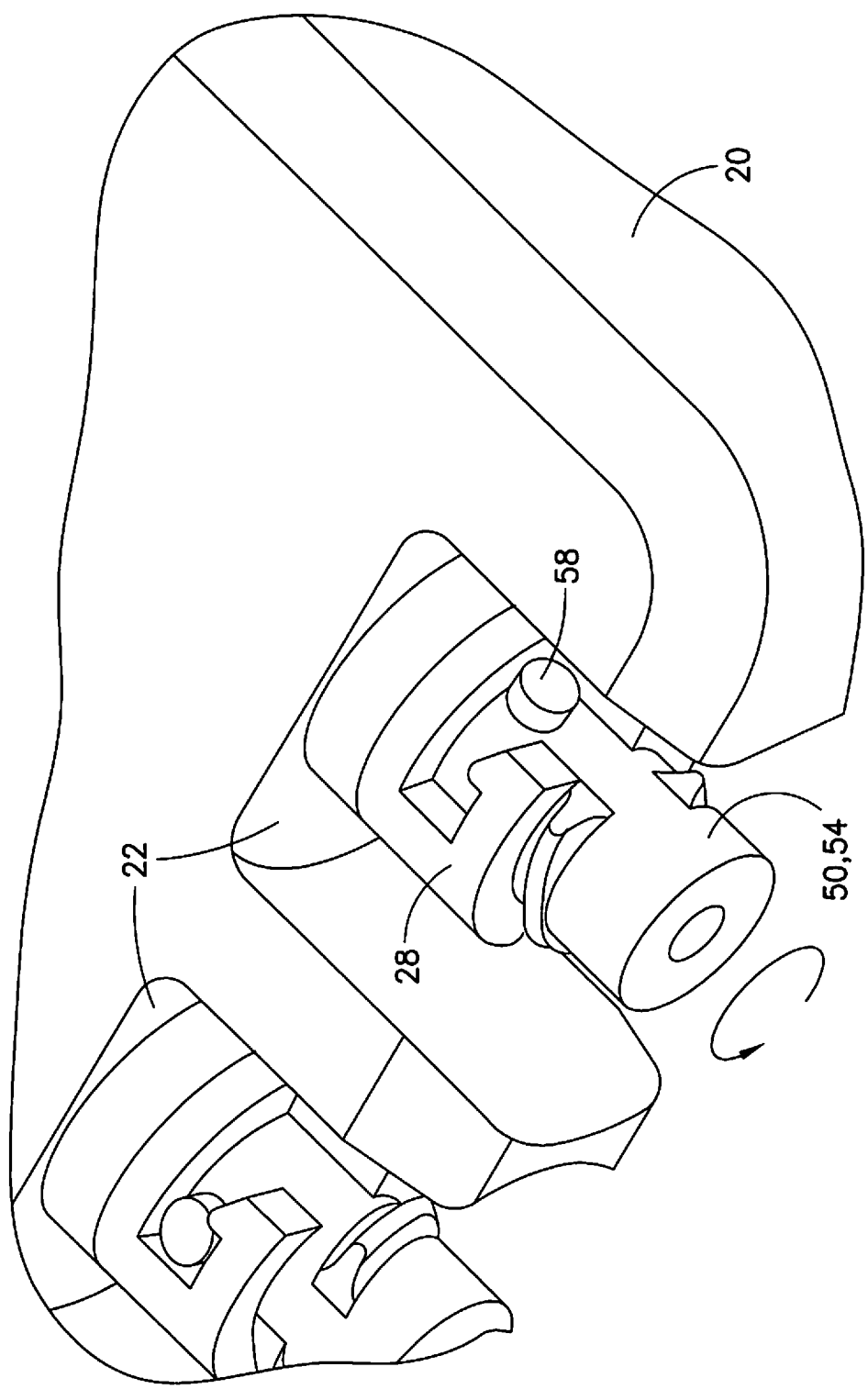
FIG. 7 illustrates a right perspective view of the needle hub in the magazine housing in an unlocked position.
Figure 8:
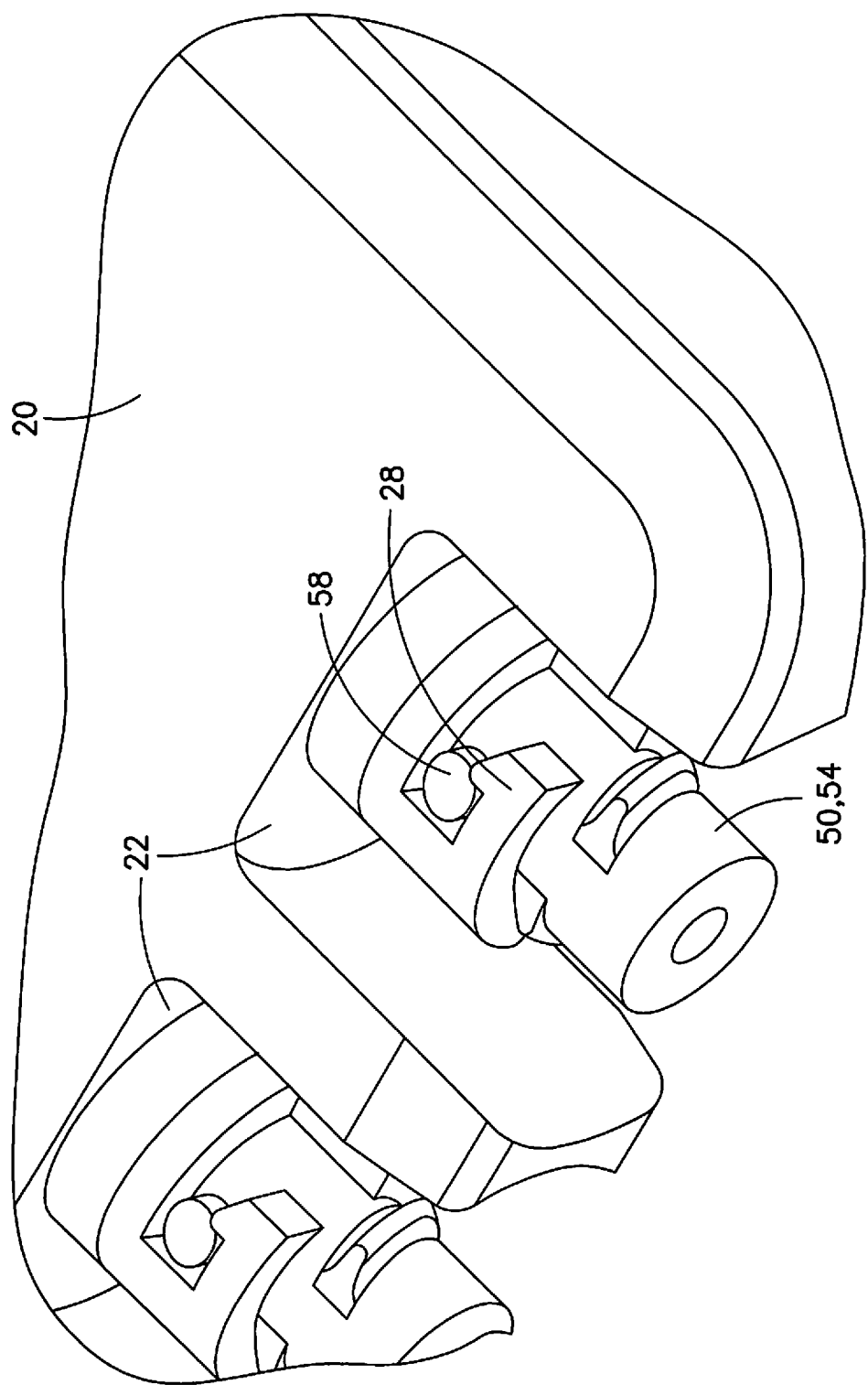
FIG. 8 illustrates a right perspective view of the needle hub in the magazine housing in a locked position.

FIG. 6 illustrates, according to one embodiment, that after the selected needle hub 52 is used for medication delivery by the medication pen 2, the medication pen 2 returns the selected needle hub 52 back to the magazine housing 20. Specifically, the selected needle hub 52 engages the connector 28 in the selected hub chamber 24 of the magazine housing 20. The selected needle hub 52 returns to the selected hub chamber 24 that it was originally sealed in. FIGS. 7 and 8 illustrate the operation of the connector 28 being a quarter turn bayonet connection engaging one of the plurality of needle hubs 50. Operation of the connector 28 is described below.

Figure 9:
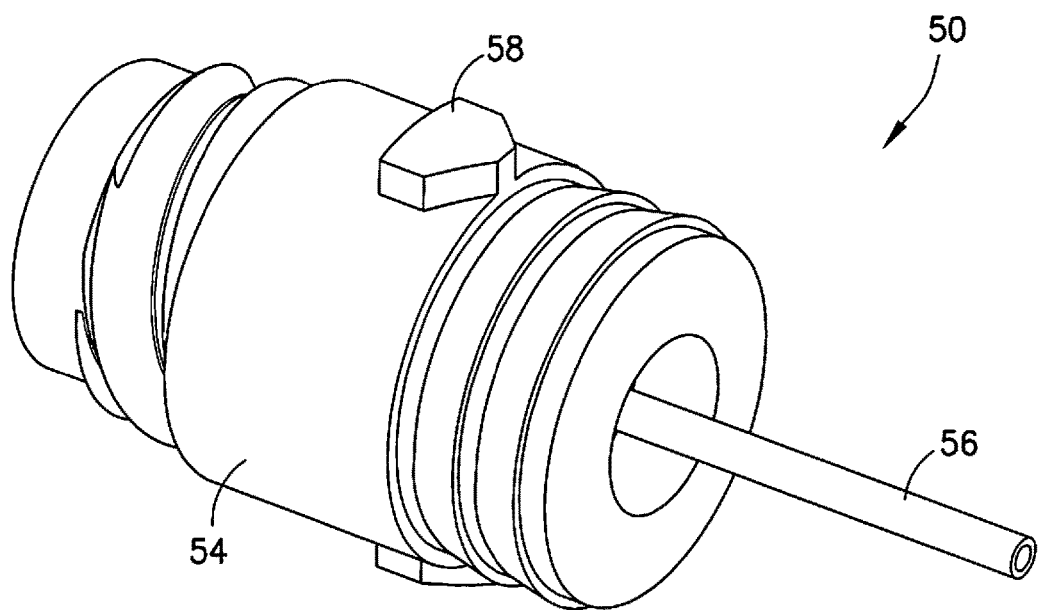
FIG. 9 illustrates a left perspective view of the needle hub.

FIG. 9 illustrates, according to one embodiment, one of the plurality of needle hubs 50. The plurality of needles hubs 50 each includes a hub body 54, a hub cannula 56 and a radial lug 58. A proximal and distal end of the hub body 54 preferably includes threads or the push-pull detent. The proximal end of the hub body 54 is configured to be attached to the adapter 4 and the distal end of the hub body 54 is configured to be attached to the connector 28 in the magazine housing 20.

The hub cannula 56 is fixed to the hub body 54 and extends from the distal end of the hub body 54. The hub cannula 56 provides a means to deliver medicament to the patient. Specifically, when one of the plurality of needle hubs 50 is connected to the medication pen 2, fluid communication is established. Accordingly, medicament travels to the needle hub 50 and exits through the hub cannula 56. Although not illustrated, the distal end of the hub cannula 56 includes a sharpened bevel cut that is configured to penetrate tissue.

The radial lug 58 is disposed adjacent to the threads or the push-pull detent at the distal end of the hub body 54. The radial lug 58 acts as a secondary retention means to the connector 28 in the magazine housing 20. Two radial lugs 58 are preferably disposed on the hub body 54 approximately 180° apart.

As illustrated in FIG. 7, when the used needle hub 50 is returned to the magazine housing 20, the used needle hub 50 engages the quarter turn connector 28 via the radial lug 58. The used needle hub 50 is then rotated approximately 90°, as illustrated in FIG. 8, to engage the quarter turn connector 28 of the magazine housing 20. Thus, the quarter turn connector 28 is secured to the needle hub 52 via the radial lug 58.

Figure 10:
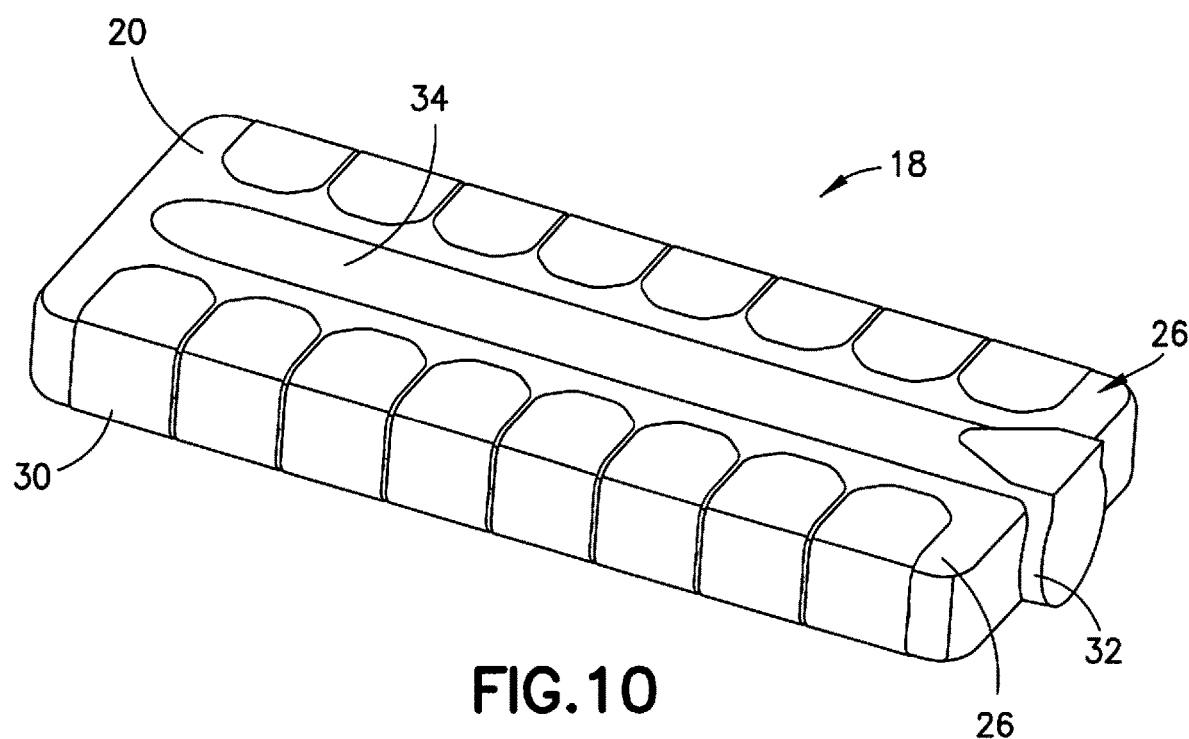
FIG. 10 illustrates another embodiment of a magazine having a storage bin.

According to another embodiment, as illustrated in FIGS. 10-13, the magazine 18 also includes a storage bin 34. FIG. 10 illustrates that the storage bin 34 is disposed between the two magazine arrays 26 in the magazine housing 20 and provides a cavity to store needle hubs 50 after use. Instead of returning the used needle hub 50 in one of the plurality of hub chambers 22 as described above, the needle hub 50 is disposed in the storage bin 34. When the used needle hubs 50 are placed in the storage bin 34, the used needle hubs 50 are inaccessible.

Figure 11:
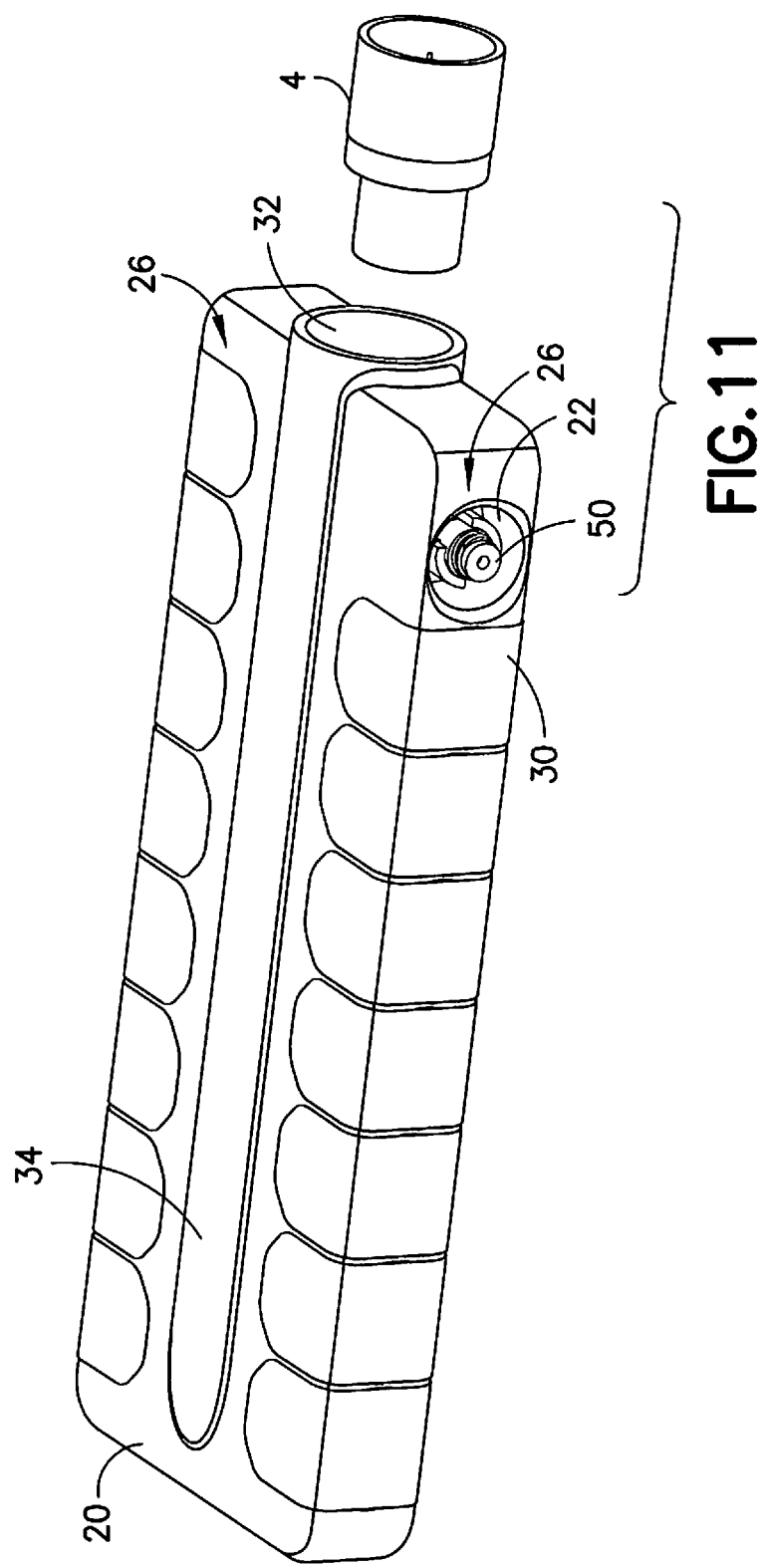
FIG. 11 illustrates the magazine of FIG. 10 with an adapter chamber.

FIG. 11 illustrates that the storage bin 34 includes an opening or adapter chamber 32 for the plurality of needle hubs 50 to access. The adapter 4 or an end cap (cover) engages the opening or adapter chamber 32 to seal the storage bin 34. The opening or adapter chamber 32 advantageously provides access to the storage bin 34, as well as provides a space to carry the adapter 4 when the adapter 4 is not in use.

The storage bin 34 is penetration resistant and leak proof. Such a configuration advantageously prevents used needle hubs 50 from piercing through the storage bin 34. Also any contaminants from the used needle hubs 50 such as blood are contained and do not escape from the storage bin 34. As a result, contaminants from the used needle hubs 50 are safely enclosed and sealed inside the storage bin 34.

As illustrated in FIG. 10, one of a plurality of peel tabs 30 is used to seal the opening or adapter chamber 32. The opening or adapter chamber 32 is preferably a larger size than the plurality of hub chambers 22. Accordingly, the peel tab 30 for the opening or adapter chamber 32 is larger than the plurality of peel tabs 30 for each of the plurality of hub chambers 22. In an alternate embodiment, the plurality of peel tabs 30 for the opening or adapter chamber 32 and the plurality of hub chambers 22 are all the same size.

Figure 12:
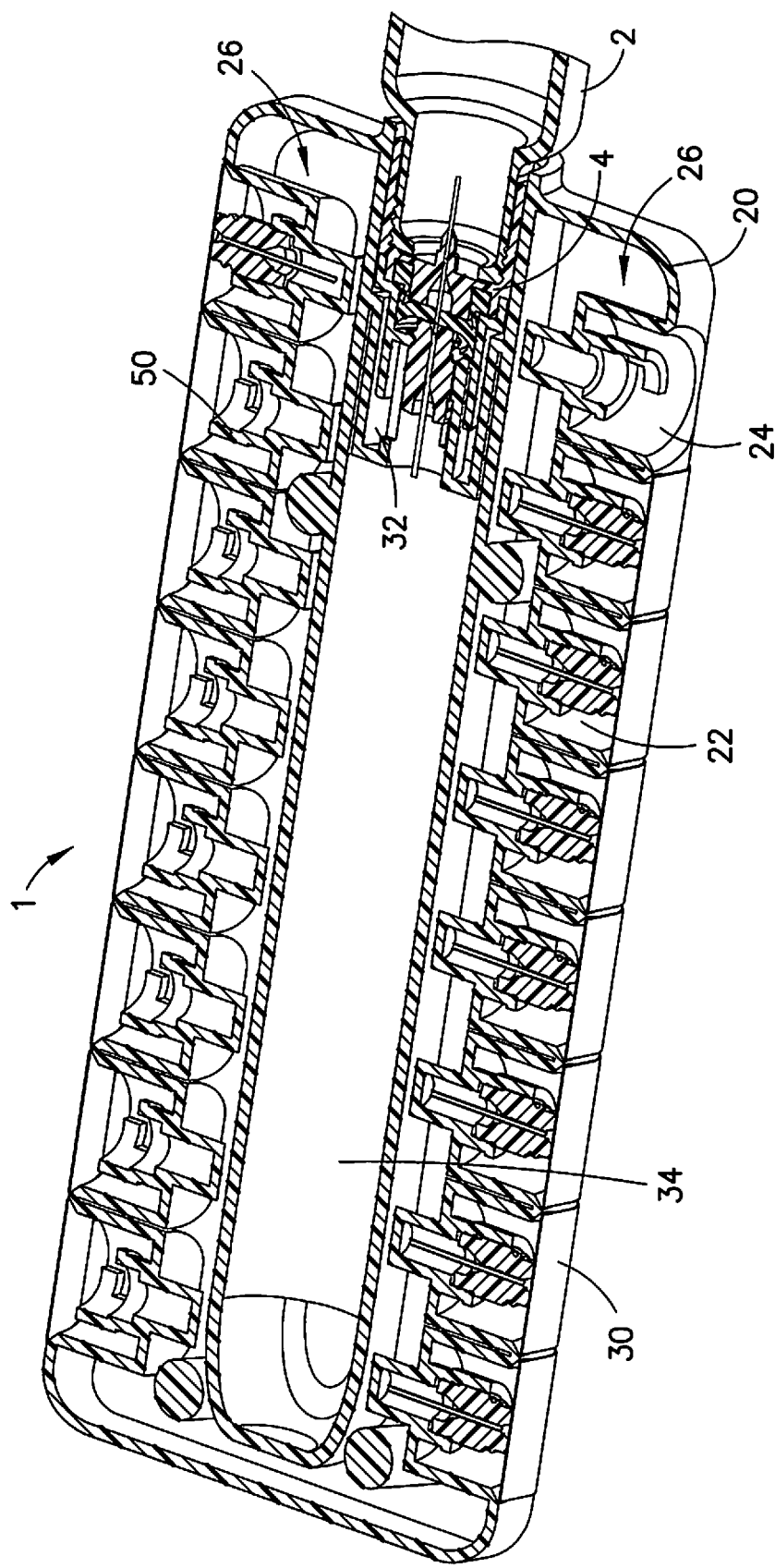
FIG. 12 illustrates a cross sectional view of the magazine assembly where the medication pen is placing a needle hub in the storage bin.

During operation, the adapter 4 is removed from the opening or adapter chamber 32 and is attached to the medication pen 2 as described above. As illustrated in FIG. 12, when one of the plurality of needle hubs 50 is used, the medication pen 2 in inserted into the opening or adapter chamber 32 to release the needle hub 50 into the storage bin 34. Specifically, the medication pen 2 overcomes a light interference fit when pushing the used needle hub 50 into the opening or adapter chamber 32 of the storage bin 34. The opening or adapter chamber 32 then engages the thread at the distal end of the hub body 54 and/or the radial lug 58. Subsequently, the medication pen 2 is rotated approximately 90° and the medication pen 2 is removed from the opening or adapter chamber 32 to disengage the needle hub 50 from the medication pen 2. The needle hub 50 is then disposed into the storage bin 34. This process repeats for each used needle hub 50. Once one of the plurality of needle hubs 50 is placed into the storage bin 34, there is no way to remove the needle hub 50. Thus, the storage bin 34 advantageously secures the plurality of needle hubs 50 after use and prevents accidental reuse.

Figure 13:
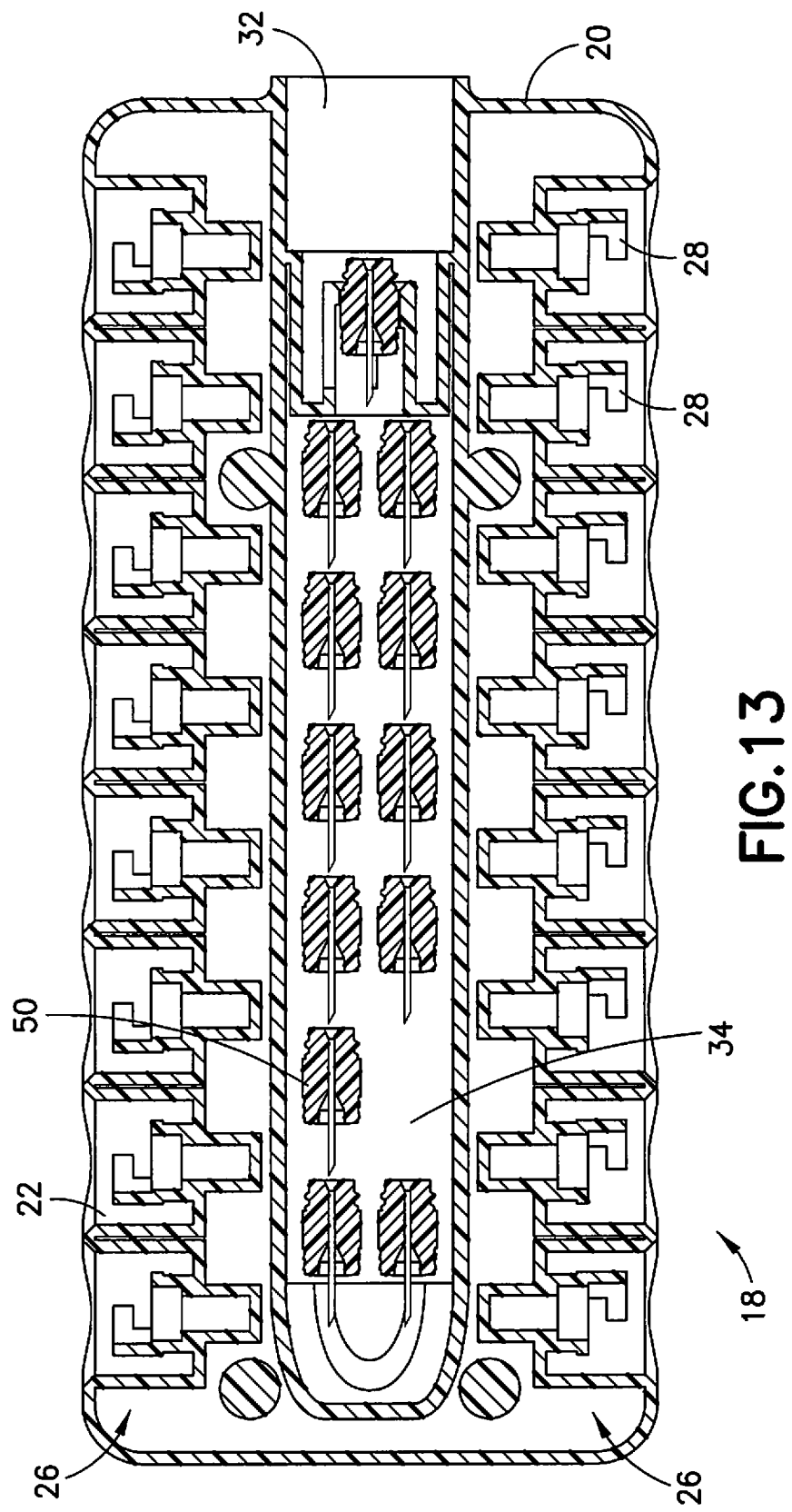
FIG. 13 illustrates a cross sectional view of the magazine assembly where a plurality of needle hubs are disposed in the storage bin.

FIG. 13 illustrates the process of repeatedly storing one of the plurality of used needle hubs 50 in the storage bin 34. After all of the plurality of needle hubs 50 is used and placed into the storage bin 34, the magazine 18 is ready for disposal.

Figure 14:
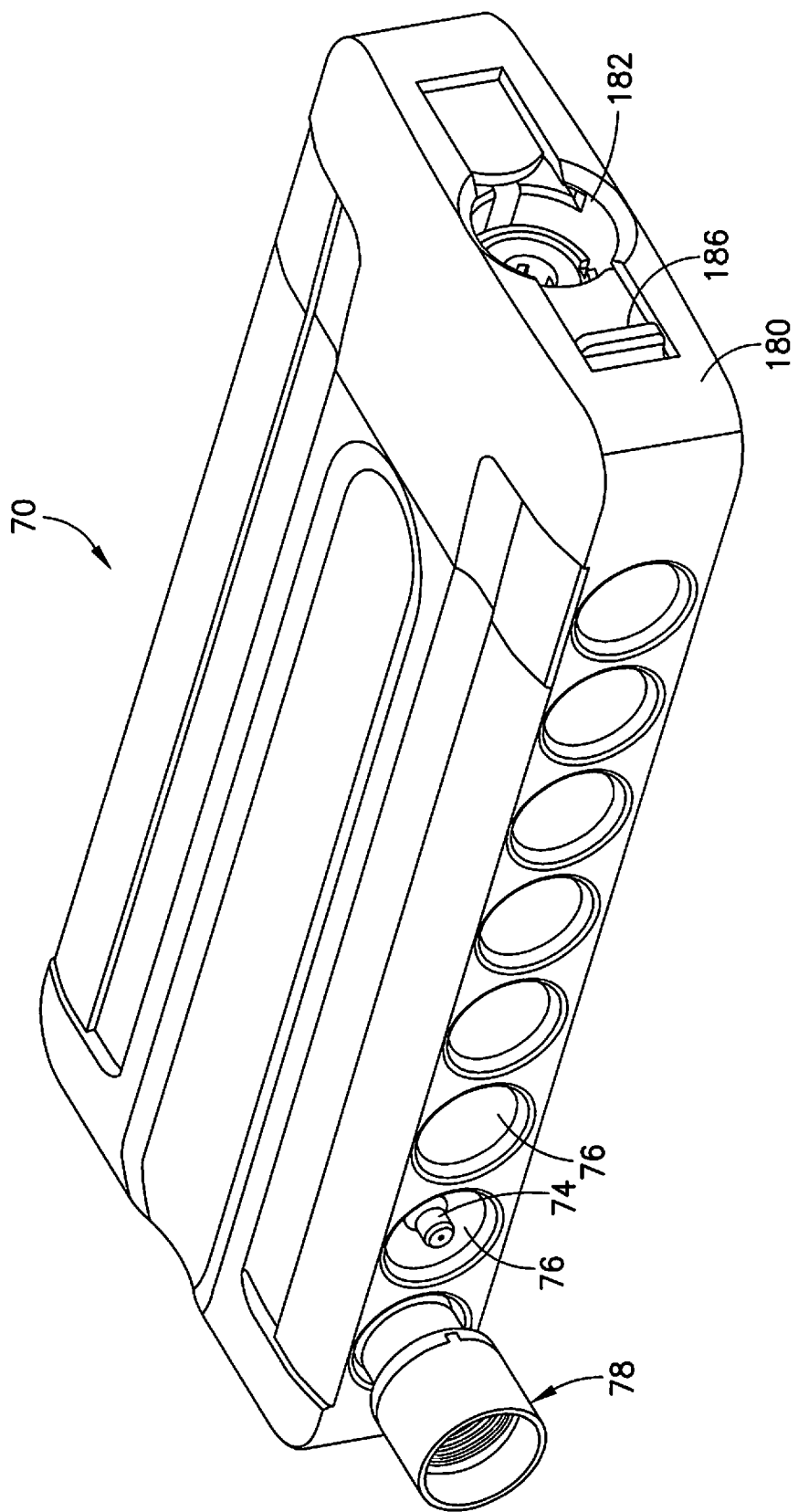
FIG. 14 illustrates a perspective view of a magazine assembly for the needle hubs in another embodiment.
Figure 15:
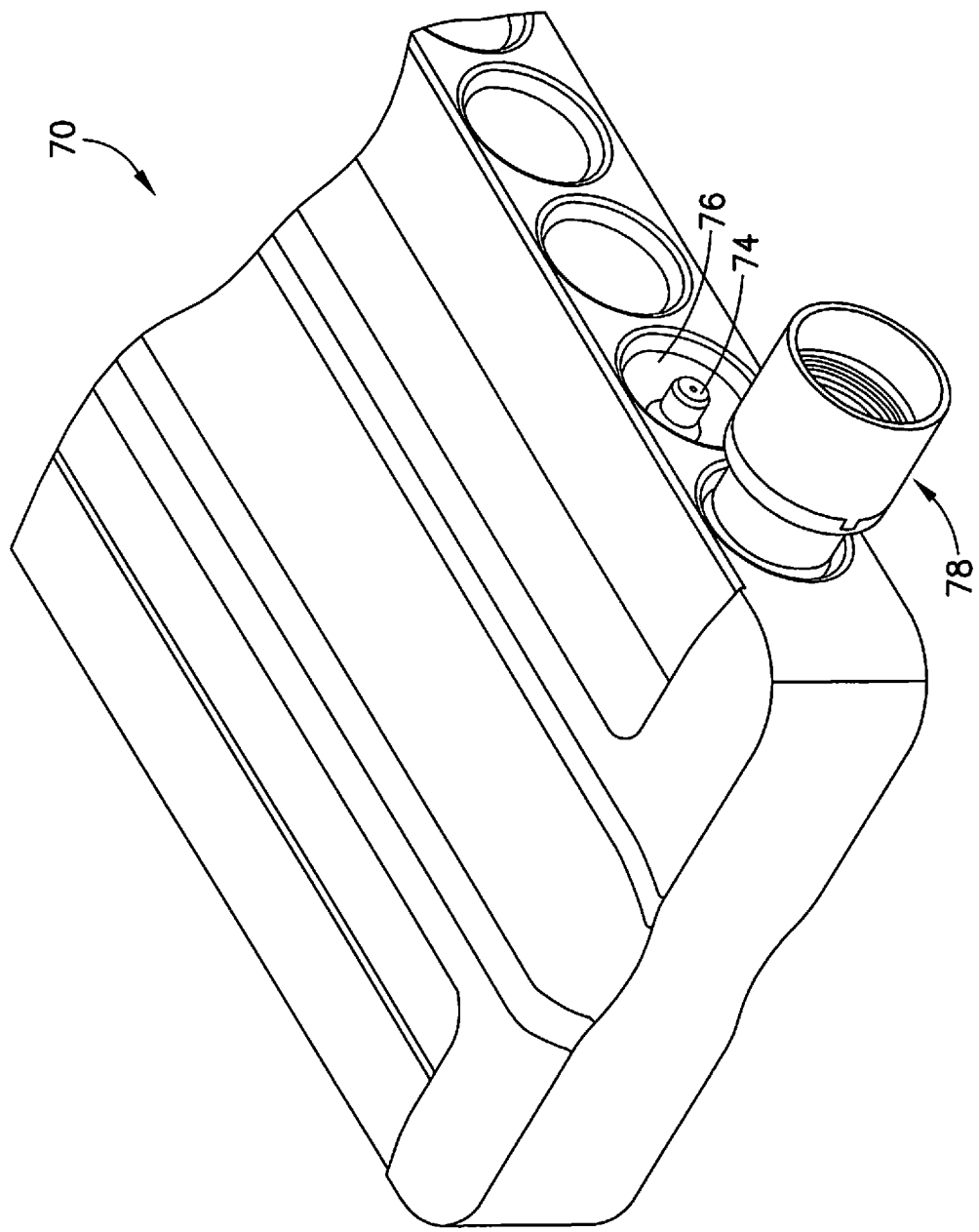
FIG. 15 is an enlarged partial view of the magazine assembly of FIG. 14.

Referring to FIGS. 14-22, another embodiment of the magazine and connector mechanism for the needle hub is shown. Referring to FIG. 14, the magazine housing 70 is similar to the previous embodiment with the exception of the connectors for the needle hubs 74. As in the previous embodiment, the housing includes a plurality of chambers 76 where each chamber stores a needle hub 74 until ready for use. The chambers 76 can have a suitable closure such as label or door as in the previous embodiment to maintain the needle hubs in a clean and sterile condition until ready for use. For ease of illustration, the covers or labels are not shown in FIGS. 14 and 15. The chambers 76 have a dimension and are oriented in a direction for being accessed by the adapter 78 for coupling the needle hub 74 to the adapter 78 and/or suitable delivery device. The chambers can be arranged in one or more arrays where a needle hub can be selected by the operator for connecting to a delivery device for injecting a substance to a patient.

Figure 16:
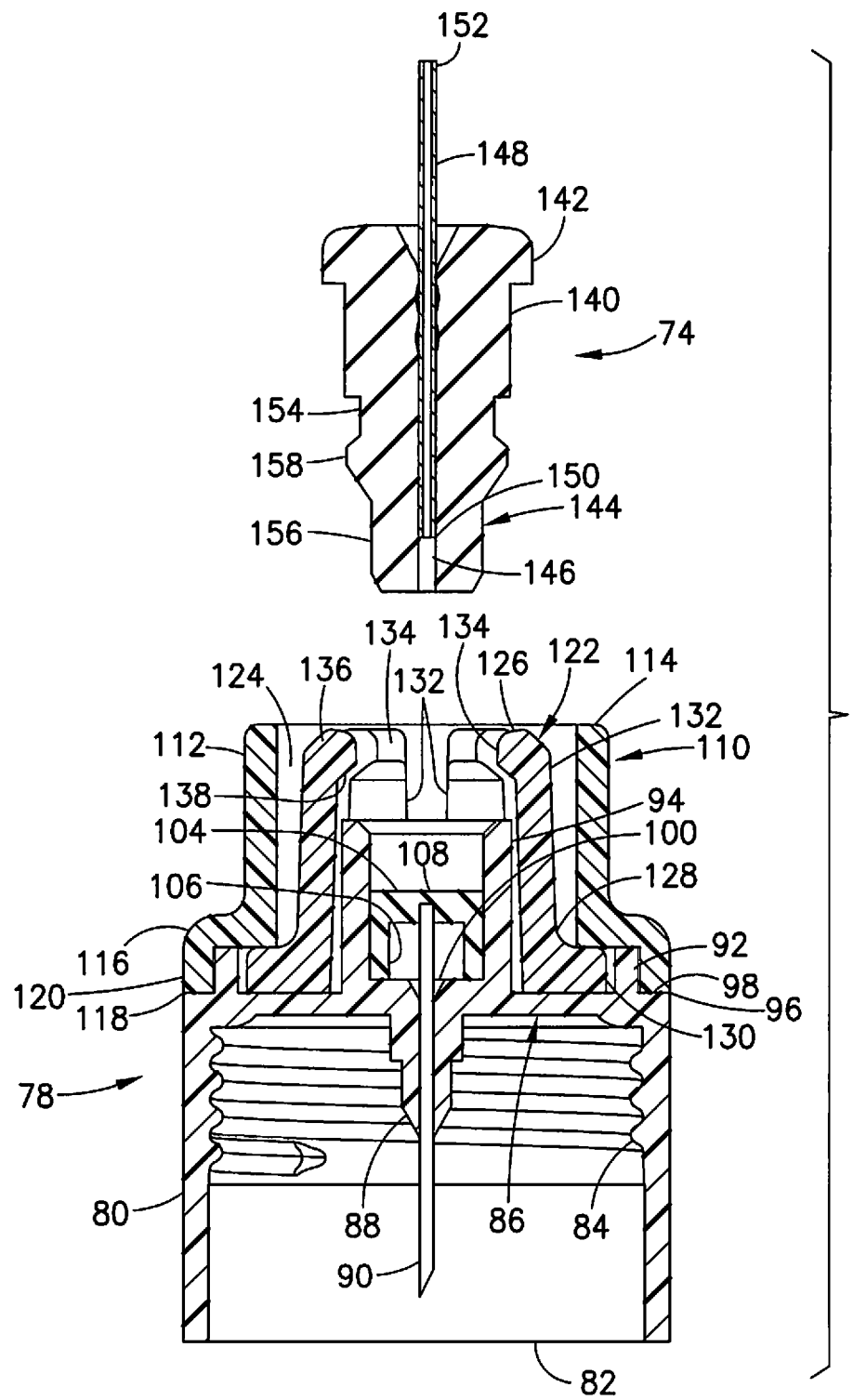
FIG. 16 is a cross sectional view of the needle hub and adapter in the embodiment of FIG. 14.

The adapter 78 is similar to the adapter of the previous embodiment and is configured for connecting to a delivery pen. Referring to FIG. 16, the adapter 78 includes a body 80 having an open end bottom end 82 with internal threads 84 for connecting to the delivery pen. The body 80 has a top end with a top wall 86 with a post 88 extending toward the open end 82 and supporting a cannula 90 for connecting with the delivery pen. The top wall 86 includes an outer ring 92 and an inner ring 94 extending axially upward and away from the top wall 86. The delivery pen is not show in FIGS. 14-22 for ease of illustration but is to be understood as corresponding to the delivery pen 2 as shown in FIGS. 3-6. In the embodiment shown, the adapter is configured for coupling with a delivery pen by a threaded connection. In other embodiments, the adapter can be connected by other mechanisms or can be integrally formed with the pen.

The outer ring 92 has an annular configuration and is spaced inwardly from an outer edge 96 of the body 80 at the top end to define an axially facing shoulder 98. The inner ring 94 is spaced inwardly from the outer ring 92 and encircles an opening 100 receiving the hub cannula 102. As shown in FIG. 16, the cannula 90 passes through the opening 100 and extends downward from the post 88 and extends upward from the top wall 86. The inner ring 94 supports a septum 104 as in the previous embodiment. The septum 104 can be pierced or penetrated by the cannula 90 in a manner similar to the previous embodiment of FIGS. 3 and 4. The septum 104 in the embodiment shown has an annular, substantially cylindrical side wall 106 received in the inner space formed by the inner ring 94 and a top wall 108 that can be pierced or penetrated by the top end of the cannula 90 when the adapter 78 is connected to the needle hub 74. In the embodiment shown in FIG. 16, the top wall 108 of the septum 104 is spaced below the top edge of the inner ring 94 so that the septum is recessed within the cavity defined by the inner ring 94.

The adapter 78 includes an outer collar 110 coupled to the top end of the body 80. The collar 110 includes an annular, cylindrical side wall 112 with a top end 114 and a skirt 116 forming an open bottom end 118. The skirt 116 has an annular flange 120 that fits over the outer ring 92 for attaching the collar 110 to the body 80. The collar 110 can be attached securely to the body 80 by a suitable coupling, adhesive, welding, friction fit, or other mechanism. As shown in FIG. 16, side wall 112 is spaced radially inward from flange 120 and spaced radially outward from inner ring 94. The side wall 112 has a substantially cylindrical configuration with an outer diameter to fit within the respective chamber 76 during the assembly of the needle hub 74 to the adapter 78.

A connecting member 122 is provided in the annular space 124 between the inner ring 94 and the side wall 112 of the collar 110 for connecting to the needle hub 74. In the embodiment shown, the connecting member 122 has a substantially cylindrical configuration surrounding the inner ring 94 with a distal end 126 and a proximal end 128. The connecting member 122 has an axial height greater than an axial height of the inner ring as shown in FIG. 16.

The proximal end 128 of connecting member 122 includes a base 130 forming a skirt that extends radially outward with a bottom face for mating with the outer face of the top wall 86 of the body 80. A top face of the base 130 is oriented to mate with a bottom face of the skirt 116 of the collar 110 to capture the connecting member 122 within the annular space 124. In the embodiment shown in FIG. 16, the base 130 has a thickness corresponding substantially to the axial height of the inner ring 94 and an outer diameter complementing an inner diameter of the inner ring 94.

Connecting member 122 includes a plurality of movable or flexible legs 132 extending axially from the base 130 to define a substantially cylindrical side wall of the connecting member 122. The top end of the legs 132 defines the distal end of the connecting member 122. Each leg 132 has a detent forming a coupling tab 134 extending radially inward with respect to the central axis of the connecting member 122 for coupling with the needle hub such as by snap fit. In the embodiment shown, the coupling tabs 134 have chamfered top edge 136 and a chamfered bottom edge 138.

The needle hub 74 in the embodiment shown has a substantially cylindrical body 140 with a flange 142 at a distal end having a connecting portion 144 at a bottom end. An axial passage 146 extends through the needle hub 74 for supporting a cannula 148. In the embodiment shown the cannula 148 has proximal end 150 received in the axial passage 146 and a distal end 152 with a tip for penetrating the skin of the patient during use. The tip as shown as a flat or blunt end although it is to be understood that the tip can be formed as a sharp, pointed or beveled tip as known in the art.

Figure 17:
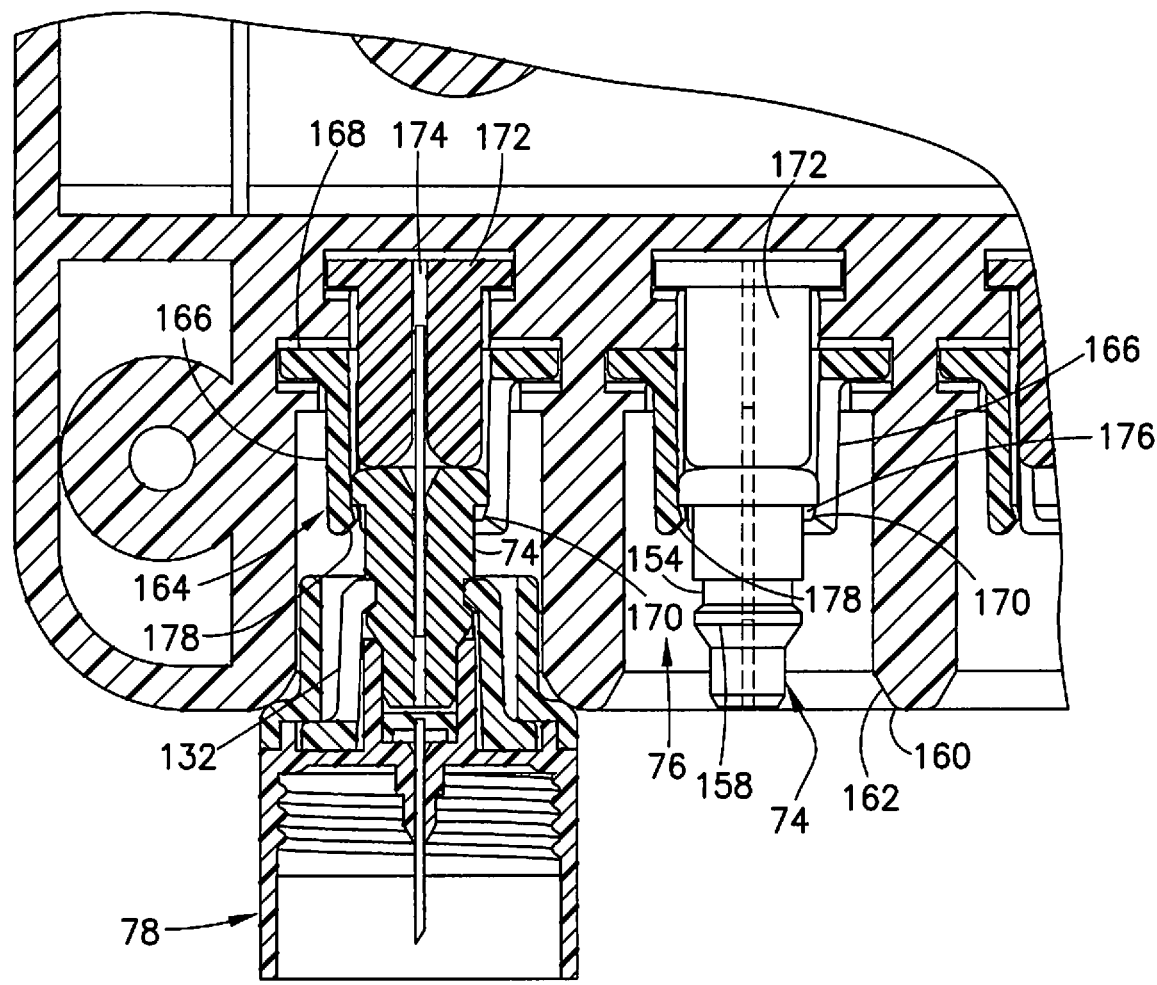
FIG. 17 is a partial view in cross section showing the adapter coupling with the needle hub within the magazine of FIG. 14.

The connecting portion 144 has at least one recess shown as an annular recess 154 extending around the circumference of the surface of the connecting portion 144 for mating with the coupling tabs 134 of the legs 132. A cylindrical axial end portion 156 of the connecting portion 144 has an outer diameter less than an outer diameter of the body 140 and forms an annular rib 158 between the cylindrical portion 156 and the annular recess 154. As shown in FIG. 17, the cylindrical end portion 156 has a dimension to pass through the opening in the connecting member 122 and fit within the inner dimension of the inner ring 94 to form a fluid tight connection with the inner ring 94 and provide a fluid connection with the cannula 90 of the hub body 80. The annular rib 158 has a dimension to mate with the inwardly extending tabs 134 of the legs 132 as shown in FIG. 17. In the embodiment shown, the adapter is coupled to the needle hub by a linear movement of the adapter relative to the needle hub without requiring rotation of the adapter relative to the needle hub.

Figure 18:
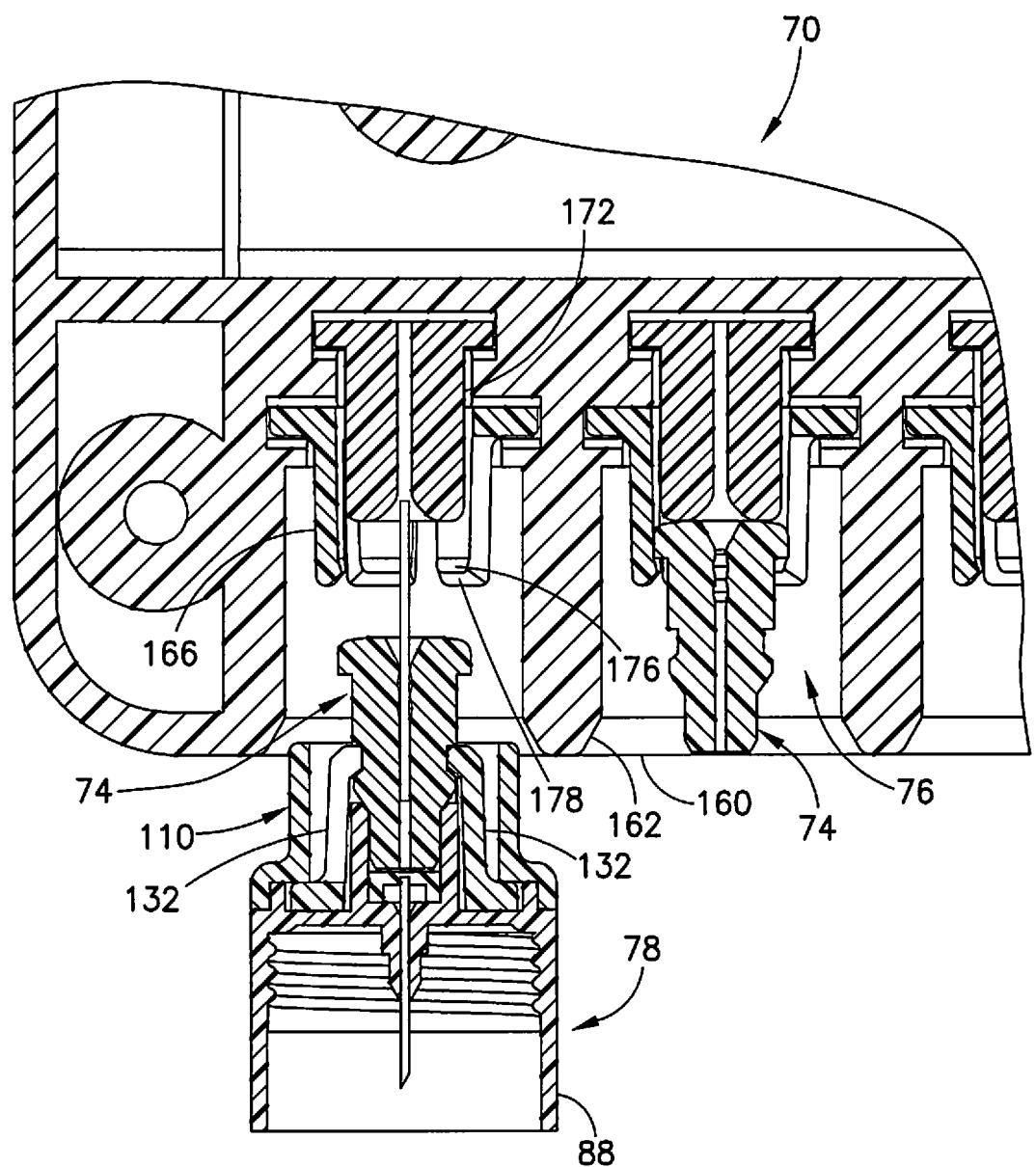
FIG. 18 is a partial view of the magazine in cross section showing the adapter removing the needle hub from the magazine.

The magazine 70 is provided with the chambers 76 for supporting the needle hub 74 until ready for use. Referring to FIG. 17, the chamber 76 has an open end 160 with a chamfered edge 162 to assist in guiding the adapter 78 into the chamber 76. The chamber 76 defines a cavity receiving a connector 164 for retaining the hub 74. In the embodiment shown, the connector 164 includes a plurality of legs 166 extending from a base 168 toward the open end of the chamber 76 and oriented around a central axis. The legs 166 can be moveable or flexible to enable coupling with the needle hub. A distal end of each leg 166 includes a coupling tab 170 extending radially inward with respect to the central axis of the connector 164. The base 168 is fixed to the magazine 70 to capture the hub until ready for use. In the embodiment shown, a cylindrical member 172 is positioned within the central opening defined by the arms 166 with an axial passage 174 to receive the cannula 148 during storage of the hub. The tabs 170 have a chamfered inner edge 176 to be able to slide over the flange 142 of the hub when the needle hub is removed from the chamber. The outer edge 178 is also chamfered as shown in FIG. 18 to allow ease of assembly of the hub onto the connector 164. In this embodiment, the needle hub can be separated by pulling the needle hub in a linear direction outwardly from the chamber without requiring rotation of the needle hub relative to the connector 164.

Figure 22:
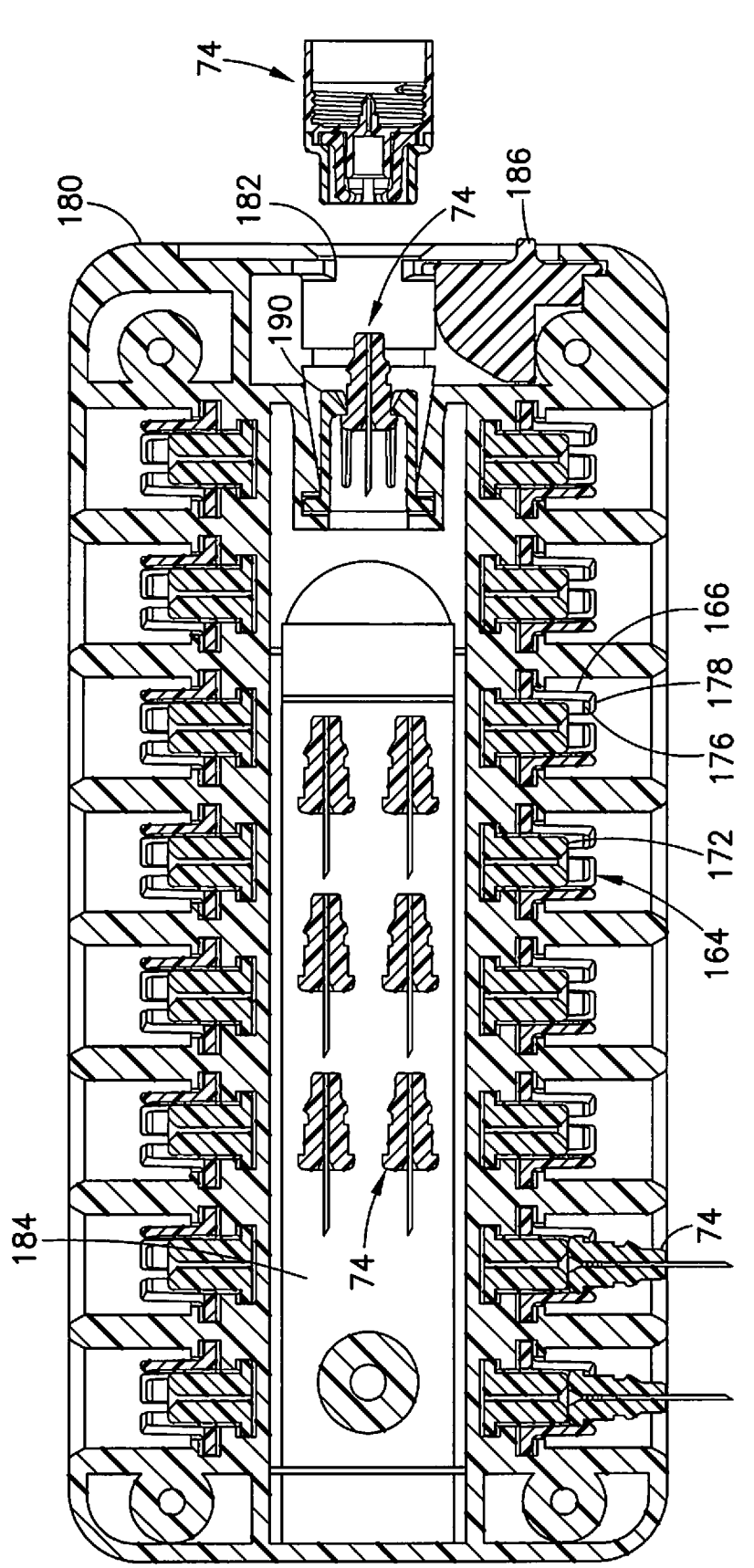
FIG. 22 is a side view in cross section showing the adapter separated from the magazine and the used needle hub retained in the magazine.

In the embodiment shown in FIG. 14, an end wall 180 of magazine 70 has an opening 182 to a storage cavity 184 shown in FIG. 22 for receiving the used needle hub 74 in a manner similar to the previous embodiment. A sliding closure or door 186 is provided to close the opening 182 when not in use. The opening 182 has a dimension for receiving the used needle hubs 74 and enabling the disconnection of the used needle hubs 74 from the delivery pen.

Figure 20:
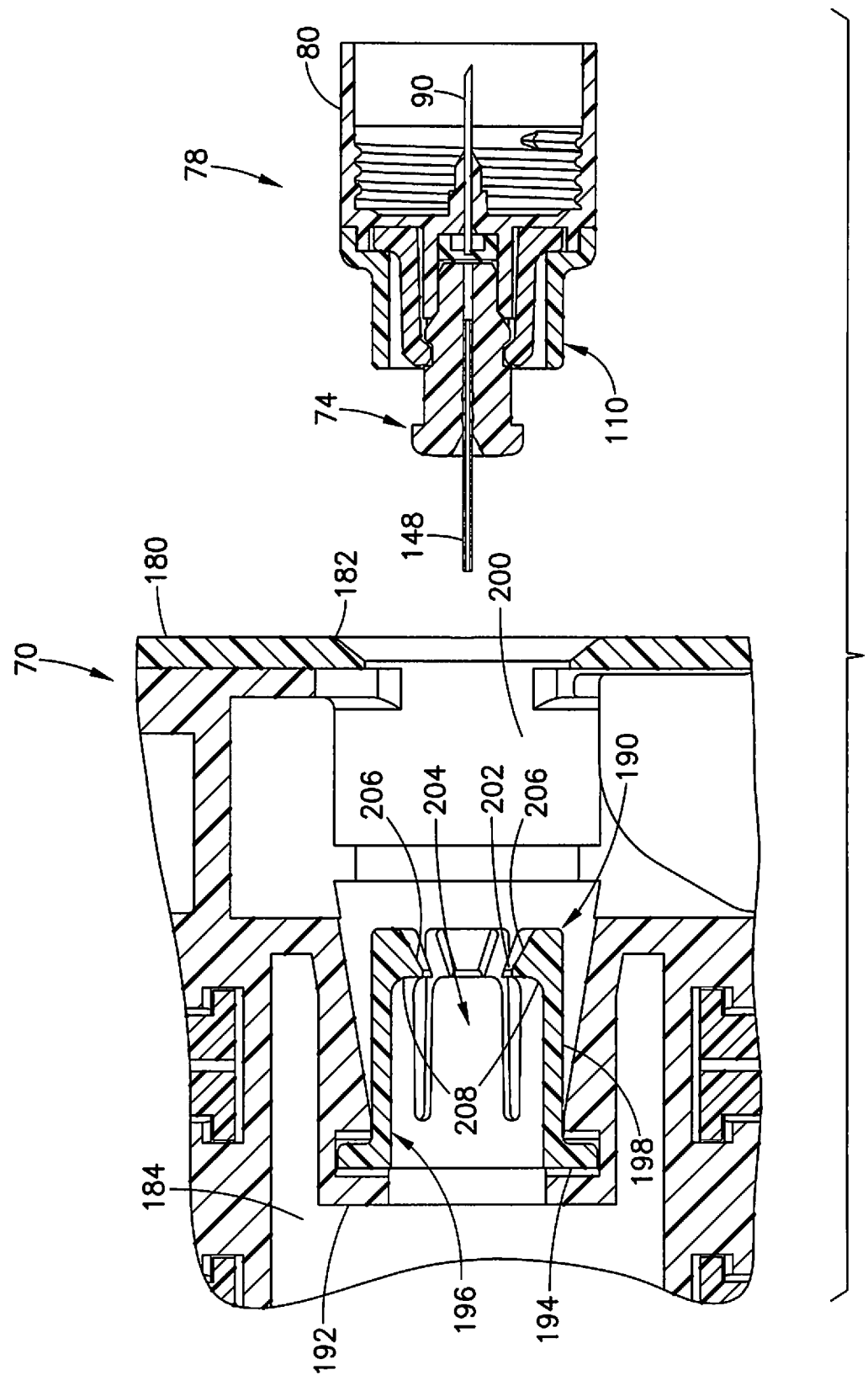
FIG. 20 is a side view in cross section showing the used needle hub aligned with the inlet opening in the magazine for receiving the used needle hub.

As shown in FIG. 20, magazine 70 includes a disconnecting assembly 190 positioned in the cavity 184 and aligned with the opening 182 for disconnecting the used needle hub 74 from the delivery pen. The assembly 190 includes a support 192 retaining a base 194 of a coupling member 196. The member 196 has a plurality of movable or flexible legs 198 extending from the base 194 toward the opening 182 and spaced below the opening 182. The legs 198 are oriented around a central axis of member 196. A chamber 200 is provided between the member 196 and the opening 182 and has a dimension for receiving the cylindrical wall of the collar 110 while allowing the used needle hub 74 to engage the assembly 190. The legs 198 include a distal end with an inwardly extending coupling detent shown as a coupling tab 202 and forming an axial passage 204. The coupling tabs 202 have an inclined chamfered top edge 206 to allow the needle hub 74 to slide over the tabs 202 and into the axial passage 204. A bottom edge 208 of the coupling tabs 202 extends radially inward with respect to the center axis of the assembly 190 and is oriented to engage the bottom face of the flange 142. In one embodiment shown, the bottom face of the flange 142 of the needle hub 74 is oriented substantially perpendicular to the center axis of the needle hub. The bottom edge of the coupling tab 202 is also oriented substantially perpendicular to the center axis of the member 190 so that the tab 202 resists passage or movement of the needle hub 74 toward the opening once gripped by the tabs 202 and prevents removal of the used needle hub 74 from the magazine through the opening 182.

Figure 19:
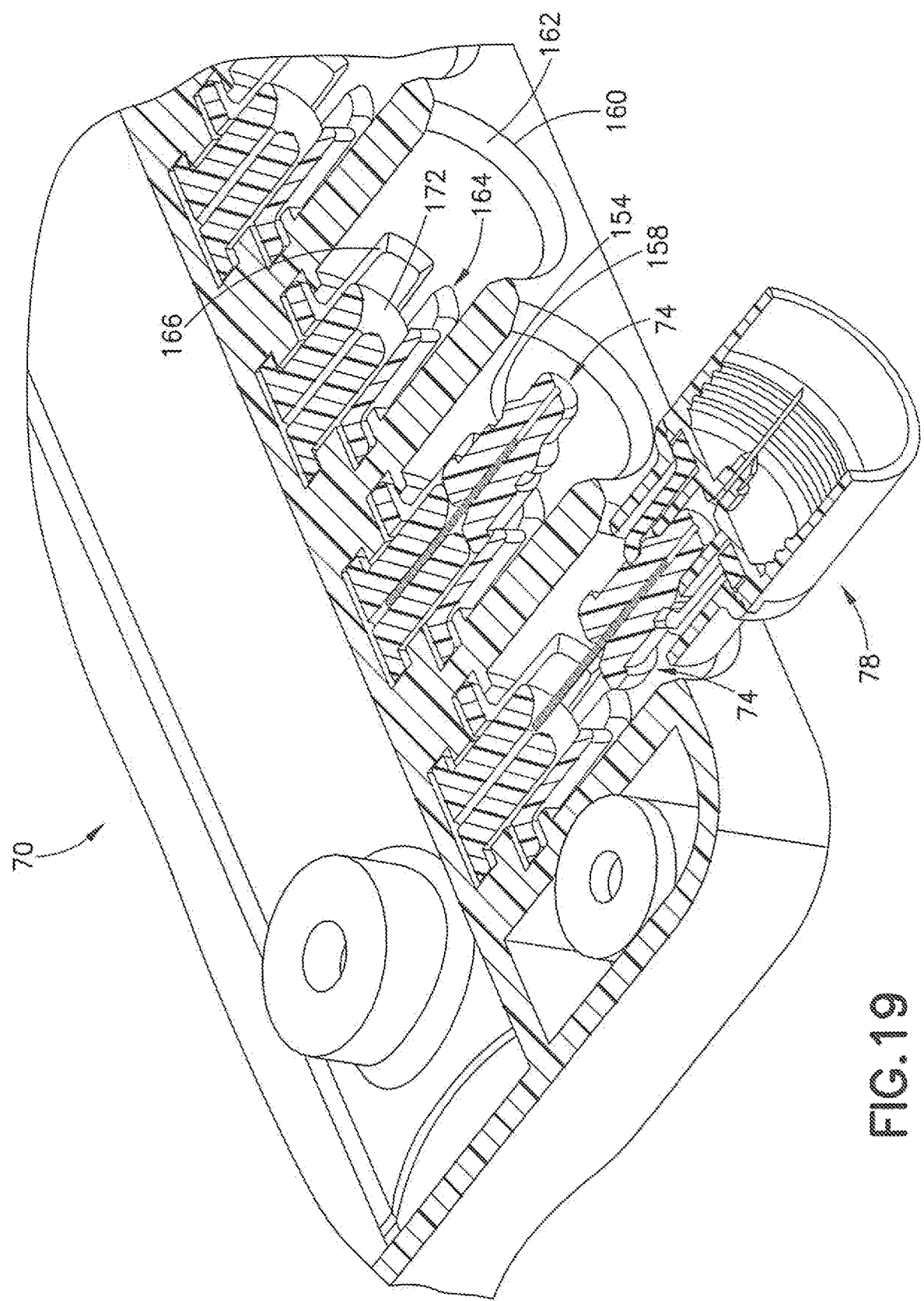
FIG. 19 is a perspective view in cross section showing the adapter removing the needle hub from the magazine.

During use, the delivery pen is connected to a selected needle hub 74 as in the previous embodiment. As shown in FIG. 17, the needle hub 74 is retained in the chamber 76 by the coupling tabs 170 on the legs 166. The cover is removed from the selected chamber containing needle hub 74 and the delivery pen with the adapter 78 is coupled to the needle hub 74 by inserting the adapter 78 into the chamber 74 and onto the end of the needle hub as shown in FIG. 17. The legs 132 of the connector 122 are sufficiently flexible so that the coupling tabs 134 slide over the inclined surface of the rib 158 for connecting the needle hub 74 to the adapter 78 by a snap fit. The delivery pen and adapter 78 are then pulled away from the magazine to remove the needle hub 74 from the chamber 76 while attached to the adapter 78. The inclined surfaces on the flexible legs 166 provide a gripping force sufficient to retain the needle hub 74 in the chamber 74 during storage but have a gripping force less than the gripping force of the legs 132 of the connecting member 122 relative to the needle hub so that the needle hub 74 can be removed from the chamber for use as shown in FIG. 18 and FIG. 19 by pulling the adapter away from the chamber. The needle hub 74 coupled to the adapter 78 as shown in FIG. 18 is ready for use by the operator.

Figure 21:
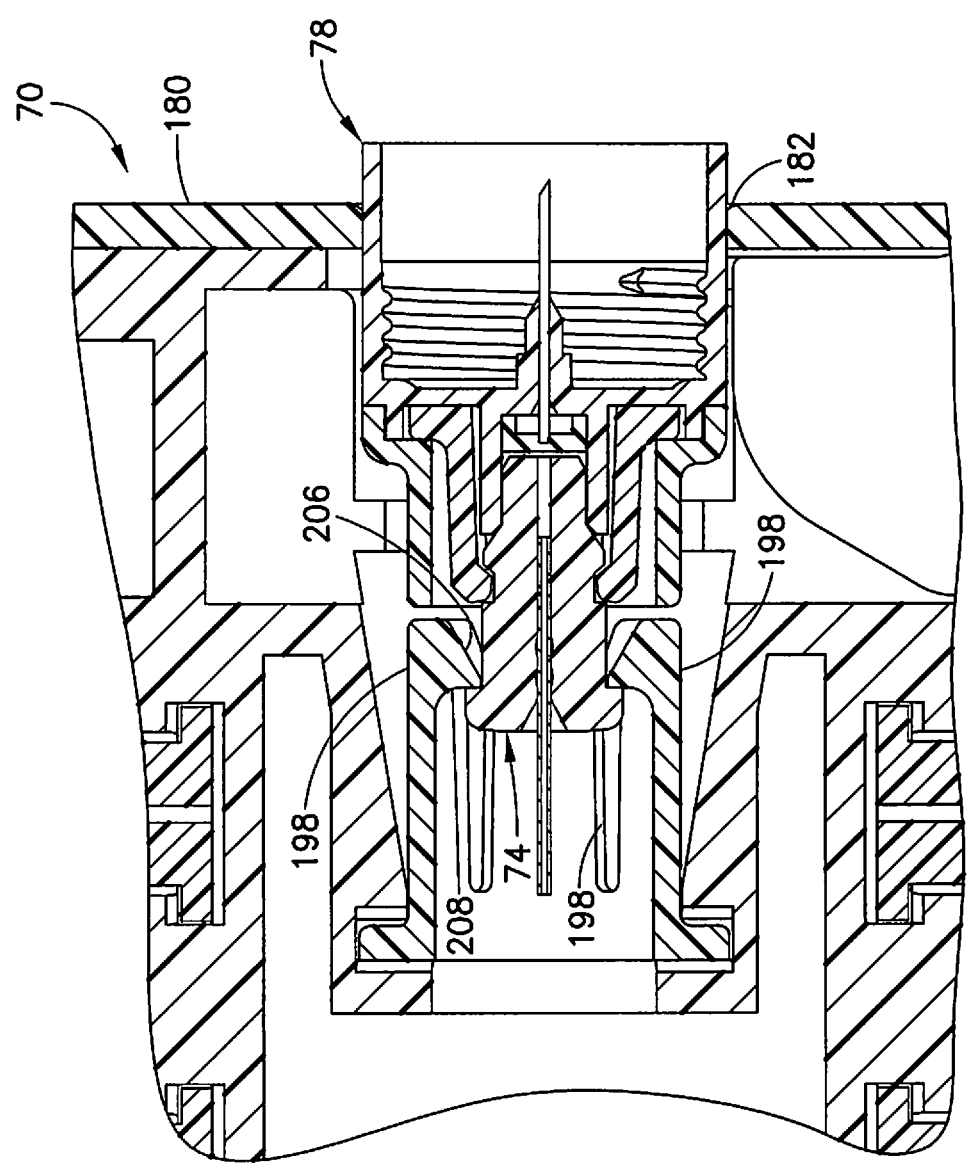
FIG. 21 is a side view in cross section showing the adapter and needle hub inserted into the opening of the magazine for coupling the needle hub to the mechanism for removing the needle hub from the adapter.

After use, the needle hub 74 can be discarded in the sharps container formed by the cavity 184 of the magazine 70. The used needle hub 74 while attached to the adapter 78 and delivery pen is inserted into the opening 182 of the magazine 70 as shown in FIG. 20 and FIG. 21. The axial end of the needle hub 74 is pushed into the opening to slide over the inclined chamfered edges 206 of the flexible legs 198. The bottom edge 208 of the legs 198 engage the bottom surface of the flange of the needle hub as shown in FIG. 21. The gripping force of the legs 198 onto the needle hub 74 is greater than the gripping force of the legs 132 of the adapter 78 relative to the needle hub so that the adapter and delivery pen separate from the needle hub 74 when pulled away as shown in FIG. 22. The used needle hubs 74 then fall into the cavity 184 of the magazine 70 as shown in FIG. 2. The door 186 can then slide to a closed position.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed, as long as they do not contradict each other. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientation descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

The invention claimed is:

1. A pen needle assembly configured to engage a medication pen for medication delivery, the pen needle assembly comprising:
   a needle hub having a fluid passage;
   an adapter having a proximal end configured for coupling to the medication pen, and a distal end configured for coupling to the needle hub;
   an adapter septum disposed between the proximal end and the distal end of the adapter; and
   an adapter cannula fixed to the adapter, wherein
   when the needle hub is not engaged to the adapter, the adapter septum is closed, and when the needle hub is engaged to the adapter, the adapter septum is open to provide fluid communication between the needle hub and the adapter.

2. The assembly of claim 1, wherein said adapter cannula pierces a proximal side of said adapter septum when said needle hub is coupled to said adapter.

3. The assembly of claim 1, wherein the adapter cannula has a distal end for piercing said adapter and providing fluid communication with the needle hub, and a proximal end for piercing a septum on the medication pen.

4. The assembly of claim 1, wherein said adapter cannula has a distal end configured to pierce said adapter septum by coupling said needle hub to said adapter.

5. The assembly of claim 4, wherein said adapter septum has a portion that is movable to contact said adapter cannula whereby said adapter cannula pierces said adapter septum.

6. The assembly of claim 4, wherein said needle hub is configured to contact said adapter septum to move at least a portion of said adapter septum toward said adapter cannula whereby said adapter cannula pierces said adapter septum.

7. The assembly of claim 4, wherein said adapter septum has a wall spaced from a distal surface of said adapter and contacts said distal surface of said adapter when said needle hub is coupled to said adapter.

8. The assembly of claim 7, wherein said distal end of said adapter cannula is oriented distally of said distal surface of said adapter.

9. The assembly of claim 4, wherein said distal end of said adapter cannula contacts said adapter septum when said needle hub is not coupled to said adapter, and said adapter cannula pierces said adapter septum when said needle hub is coupled to said adapter.

10. The assembly of claim 9, wherein said distal end of said adapter cannula is received in a proximal end of said needle hub when said needle hub is coupled to said adapter.

11. The assembly of claim 1, wherein said needle hub has a distal end and a proximal end, and a connector at said proximal end, and wherein said adapter has a distal end with a connector for coupling with said connector of said needle hub.

12. The assembly of claim 11, wherein said connector of said needle hub includes an outwardly extending rib, and said connector of said adapter has a recess for receiving said rib.

13. The assembly of claim 1, wherein said adapter septum is compressible by contact with said needle hub whereby said adapter cannula pierces said septum.

14. The assembly of claim 1, wherein said distal end of said adapter has an opening configured for receiving a proximal end of needle hub, and where said adapter septum and said adapter cannula are spaced proximally from said distal end of said adapter in said opening.

15. A pen needle assembly configured to engage a medication pen for medication delivery, the assembly comprising:
   a needle hub having a fluid passage, a cannula extending from a distal end, a proximal end, and a proximal coupling member at said proximal end;
   an adapter having an open proximal end configured for coupling to the medication pen, and a distal end configured for coupling to the proximal coupling member of said needle hub and an adapter septum disposed between the proximal end and the distal end of the adapter body, and an adapter cannula fixed to the adapter, wherein
   when the needle hub is not engaged with the adapter, the adapter septum is closed, and when the needle hub is engaged to the adapter, the adapter cannula extends through said adapter septum to provide fluid communication between said needle hub and said adapter.

16. The pen needle assembly of claim 15, wherein said adapter cannula has a distal end for piercing said adapter septum and a proximal end for piercing a septum on the medication pen.

17. The pen needle assembly of claim 15, wherein said adapter septum includes a flexible top wall configured for contacting said proximal end of said needle hub when said needle hub is connected to said adapter.

18. The pen needle assembly of claim 17, wherein said adapter septum is pierced by said adapter cannula when said needle hub is connected to said adapter.

19. The pen needle assembly of claim 15, wherein said adapter cannula is oriented on a proximal side of said adapter septum.

* * * * *